United States Patent
Miller et al.

(10) Patent No.: US 10,056,790 B2
(45) Date of Patent: Aug. 21, 2018

(54) WIRELESS TRANSFER STATION FOR TRANSFERRING ENERGY

(71) Applicant: ENOVATE MEDICAL, LLC, Murfreesboro, TN (US)

(72) Inventors: David R. Miller, Murfreesboro, TN (US); Joseph Moody, American Fork, UT (US); Allen Kilbourne, Canton, MI (US)

(73) Assignee: Enovate Medical LLC, Murfreesboro, TN (US)

( * ) Notice: Subject to any disclaimer, the term of this patent is extended or adjusted under 35 U.S.C. 154(b) by 642 days.

(21) Appl. No.: 14/323,372

(22) Filed: Jul. 3, 2014

(65) Prior Publication Data

US 2015/0365136 A1 Dec. 17, 2015

Related U.S. Application Data

(60) Provisional application No. 62/010,921, filed on Jun. 11, 2014.

(51) Int. Cl.
*H01F 27/42* (2006.01)
*H01F 37/00* (2006.01)
*H01F 38/00* (2006.01)
*H02J 50/80* (2016.01)
*H02J 5/00* (2016.01)
(Continued)

(52) U.S. Cl.
CPC ........... *H02J 50/80* (2016.02); *H01M 2/1022* (2013.01); *H01M 2/1264* (2013.01); *H01M 2/348* (2013.01); *H01M 10/46* (2013.01); *H01M 10/482* (2013.01); *H01M 10/486* (2013.01); *H01M 10/658* (2015.04); *H01M 10/659* (2015.04); *H02J 5/005* (2013.01); *H02J 7/007* (2013.01); *H02J 7/0021* (2013.01); *H02J 7/0044* (2013.01); *H02J 7/0047* (2013.01); *H02J 7/025* (2013.01); *H02J 17/00* (2013.01); *H02J 50/10* (2016.02); *H02J 50/12* (2016.02); *H02J 50/40* (2016.02); *H02J 50/50* (2016.02); *H04B 5/0037* (2013.01); *H04Q 9/00* (2013.01); *G01V 3/12* (2013.01); *H01M 2200/10* (2013.01); *H01M 2200/103* (2013.01); *H01M 2220/30* (2013.01); *H04B 5/0081* (2013.01); *Y10T 307/469* (2015.04)

(58) Field of Classification Search
CPC .. H02J 50/10; H02J 50/40; H02J 50/80; H02J 5/005; H02J 7/025; H02J 17/00
USPC ......................................................... 307/104
See application file for complete search history.

(56) References Cited

U.S. PATENT DOCUMENTS 8,663,106 B2   3/2014  Stivoric et al.
2007/0103110 A1*  5/2007  Sagoo .................... H02J 7/025
                                                       320/109
(Continued)

*Primary Examiner* — Carlos Amaya
(74) *Attorney, Agent, or Firm* — Waller Lansden Dortch & Davis, LLP; Matthew C. Cox

(57) ABSTRACT

A technology for a wireless transfer station that is operable to wirelessly transfer energy. Energy can be wirelessly transferred with a device or another wireless transfer station using an energy transfer platform having at least one surface. The energy transfer platform can comprise a plurality of wireless transfer coils, wherein the plurality of wireless transfer coils include at least one resonant charging coil and at least one inductive charging coil. Controlling a plurality of wireless transfer coils using a power management module.

10 Claims, 30 Drawing Sheets

(51) Int. Cl.
*H02J 7/02* (2016.01)
*H02J 50/12* (2016.01)
*H01M 10/658* (2014.01)
*H01M 10/659* (2014.01)
*H01M 2/10* (2006.01)
*H01M 2/12* (2006.01)
*H01M 2/34* (2006.01)
*H01M 10/48* (2006.01)
*H02J 7/00* (2006.01)
*H04B 5/00* (2006.01)
*H02J 17/00* (2006.01)
*H04Q 9/00* (2006.01)
*H01M 10/46* (2006.01)
*H02J 50/10* (2016.01)
*H02J 50/40* (2016.01)
*H02J 50/50* (2016.01)
*G01V 3/12* (2006.01)

(56) References Cited

U.S. PATENT DOCUMENTS

| | | |
|---|---|---|
| 2012/0249051 A1 | 10/2012 | Son et al. |
| 2013/0026981 A1 | 1/2013 | Van Der Lee |
| 2013/0117595 A1 | 5/2013 | Murawski et al. |
| 2013/0241474 A1 | 9/2013 | Moshfeghi |
| 2014/0001874 A1* | 1/2014 | Nahidipour ............ H02J 17/00 307/104 |
| 2014/0002014 A1 | 1/2014 | Sultenfuss et al. |
| 2015/0137746 A1* | 5/2015 | Lee ..................... H02J 5/005 320/108 |
| 2016/0254705 A1* | 9/2016 | Jung ...................... H02J 50/12 307/104 |

* cited by examiner

WIRELESS TRANSFER STATION FOR TRANSFERRING ENERGY

This application claims the benefit of and hereby incorporates by reference U.S. Provisional Patent Application Ser. No. 62/010,921,filed Jun. 11, 2014.

BACKGROUND

With an increase of electrical devices used in the transportation and communication markets, the energy industry is continually expanding to meet an increasing energy need. A large amount of time and expense can be expended to route wiring and install power outlets in a building to provide energy to electronic devices. Even with all of the time and expense spent routing wires and installing power outlets in buildings, power cords are often run along floors, walls, or baseboards of buildings to provide energy to devices. The power cords can be cumbersome to move and can present safety hazards.

To minimize safety hazards, minimize the time and expense of routing wires and installing power outlets during construction, and to provide greater mobility of devices, portable electronic devices or electronic devices not located near a convenient wired energy source can be configure to receive energy from a portable energy source, such as a battery. The portable energy source can enable a user to operate the electronic device without the need for additional building infrastructure.

Traditionally, a rechargeable battery can be recharged by physically coupling electrical contacts of the portable electronic device or electrical contacts of the rechargeable battery with an external energy source, such as a power unit connected to a wall power outlet. More recently, wireless charging has been developed to reduce the inconvenience of requiring a physical connection to recharge the rechargeable battery.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein.

Figure 1:
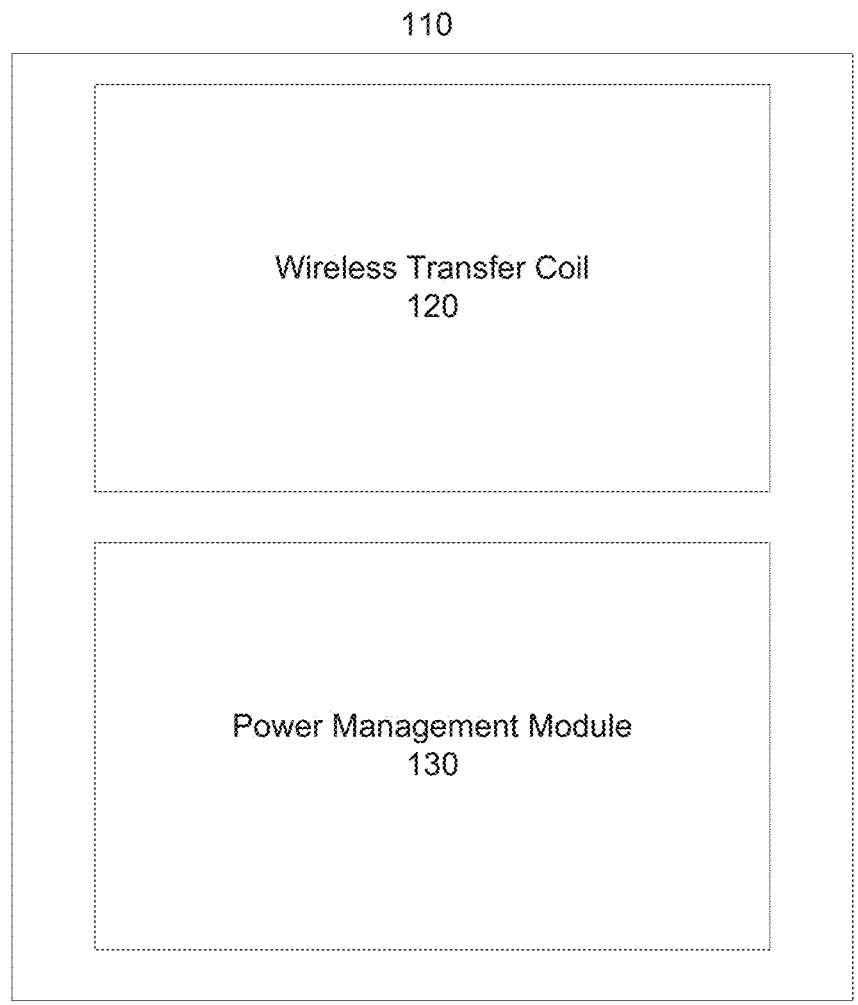
FIG. 1 depicts a wireless transfer station in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

The terms battery, cell, and/or battery cell as used herein can be used interchangeably and can refer to any of a variety of different cell chemistries and configurations. In one embodiment the cell chemistries and configurations can include, but are not limited to, lithium ion (e.g., lithium iron phosphate, lithium cobalt oxide, other lithium metal oxides, etc.), lithium ion polymer, nickel metal hydride, nickel cadmium, nickel hydrogen, nickel zinc, silver zinc, or other battery type or configurations.

The term battery pack as used herein can refer to one or more individual batteries contained within a single piece housing or a multiple piece housing. The one or more individual batteries can be electrically interconnected in parallel and/or in series to achieve a selected energy level (such as a voltage level or a current level) and capacity level.

An increasing number and variety of electronic devices are powered using non-wired energy sources, such as batteries or wireless energy sources that provide power directly to the device or to energy storage systems. The electronic devices can range from mobile phones, portable music players, laptop computers, and tablet computers to medical devices such as hearing aids, pace makers, wheeled medical carts, medical measurement equipment, medical test equipment, and other types of medical equipment.

Often, rechargeable batteries are used as a replenishable energy source for electronic devices. In one embodiment, a battery pack can include one or more rechargeable batteries. In one example, the one or more rechargeable batteries can be a lead-based battery, a lithium-based battery, a nickel based battery, or another type of chemical storage battery. Traditionally, a rechargeable battery pack provides energy to an electronic device using physical electrically conductive connections between the rechargeable battery pack and the electronic device. When the traditional rechargeable batteries of the rechargeable battery pack are depleted, the rechargeable batteries can be replenished by connecting physical electrically conductive contacts between the rechargeable battery pack and a battery charger.

In one embodiment of the present invention, a wireless transfer station can receive energy and/or send energy to another device, such as another wireless transfer station, using a wireless energy transfer scheme (e.g. transfer energy without wires). A wireless energy transfer scheme can be any form of wireless energy transfer associated with the use of electric fields, magnetic fields, electromagnetic fields, and so forth that allows electrical energy to be transmitted between two or more wireless transfer elements without using physical electrical contacts. In one example, a wireless energy transfer of wireless energy can be a transfer of electrical energy from an energy source to an electrical load without the use of interconnecting wires or physical electrical contacts.

In one embodiment, the wireless transfer station can include one or more wireless transfer coils to transfer energy and/or data with other wireless transfer stations. The wireless transfer coil can include one or more power management modules to control the energy transfers and/or data transfers with the other wireless transfer stations.

Examples of a wireless transfer station includes a wireless energy rechargeable battery pack, a wireless energy transfer platform and/or data transceiver integrated into a medical cart, a wireless energy transfer platform and/or data transceiver integrated into an electronic device, a wireless energy transfer platform and/or data transceiver integrated into a piece of furniture, a wireless energy transfer platform and/or data transceiver integrated into a plate mounted to a wall, a wireless energy transfer platform and/or data transceiver integrated into a device (such as a medical device or medical equipment), and so forth.

In one example, the wireless transfer station can be a wireless energy battery pack that can be attached to a device, such as a medical cart or medical equipment. The wireless transfer station that transfers energy and/or data with the device can also relay the energy and/or data with other devices and/or wireless transfer stations. These examples are not intended to be limiting. The wireless transfer station can be implemented in a variety of electronic devices and mounting locations.

In one embodiment, the wireless transfer station can receive data from and/or send data or information to another device, such as another wireless transfer station, using a wireless data transfer scheme. In another embodiment, the wireless data transfer scheme can be any form of data transfer associated with a communications network. In another embodiment, the communications network can be a cellular network. The cellular network can be configured to operate based on a cellular standard, such as the third generation partnership projection (3GPP) long term evolution (LTE) Rel. 8, 9, 10, 11,or 12 standard, or the institute of electronic and electrical engineers (IEEE) 802.16p, 802.16n, 802.16m-2011, 802.16h-2010, 802.16j-2009, or 802.16-2009 standard.

In another embodiment, the communications network can be a wireless local area network (such as a wireless fidelity network (Wi-Fi)) that can be configured to operate using a standard such as the IEEE 802.11-2012, IEEE 802.11ac, or IEEE 802.11ad standard. In another embodiment, the communications network can be configured to operate using a Bluetooth standard such as Bluetooth v1.0, Bluetooth v2.0, Bluetooth v3.0, or Bluetooth v4.0.In another embodiment, the communications network can be configured to operate using a ZigBee standard, such as the IEEE 802.15.4-2003 (ZigBee 2003), IEEE 802.15.4-2006 (ZigBee 2006), or IEEE 802.15.4-2007 (ZigBee Pro) standard. In another embodiment, the wireless data transfer scheme can be any form of data transfer associated with electric fields, magnetic fields, or electromagnetic fields that is transmitted between two or more wireless transfer elements without using physical electrical contacts.

In one embodiment, the wireless transfer station can include one or more wireless transfer elements. In one example, a wireless transfer element can be a wireless transfer coil. In one embodiment, the wireless transfer coil can be a coil used for transmitting and/or receiving energy and/or data using magnetic inductance and/or magnetic resonance.

FIG. 1 illustrates a wireless transfer station 110. FIG. 1 further illustrates that the wireless transfer station 110 can include a wireless transfer coil 120 and a power management module 130. In one example, the power management module 130 can convert energy received from an energy source, such as another wireless transfer station or an alternating current (AC) energy outlet, a selected current level, a selected voltage level, and/or a selected wattage level. In another embodiment, the wireless transfer station 110 can include one or more batteries, such as rechargeable batteries. In one embodiment, the wireless transfer coil 120 can comprise a transmitting coil and/or a receiving coil.

Figure 2:
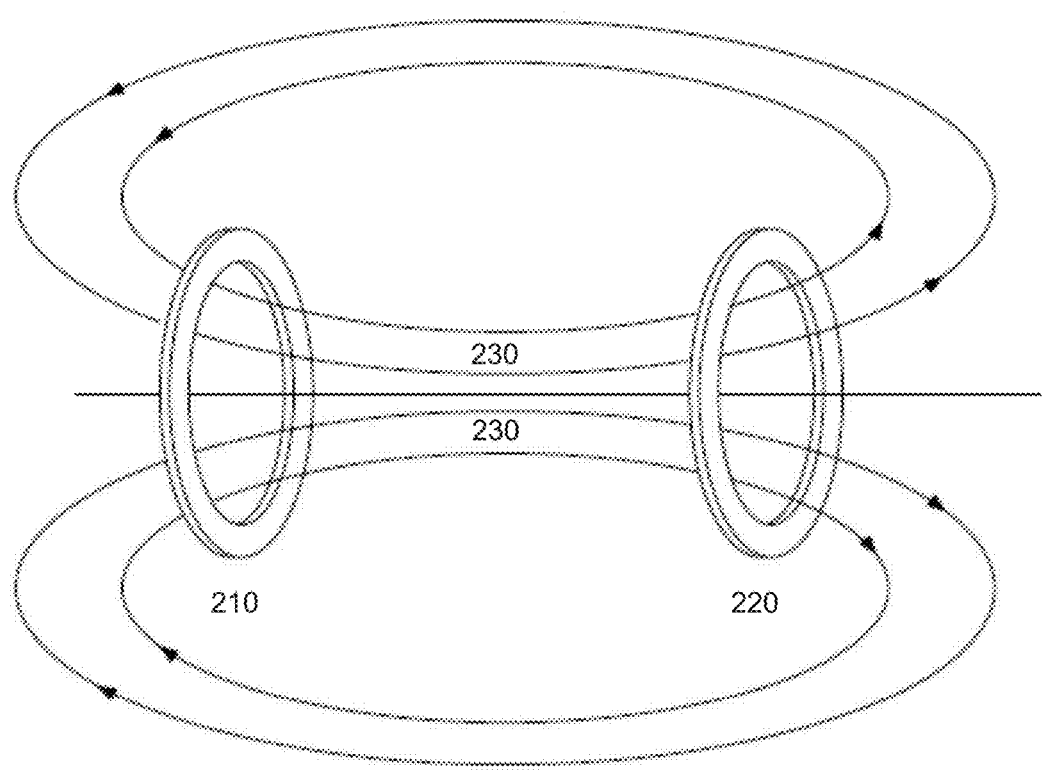
FIG. 2 depicts transferring energy or data between a plurality of wireless transfer coils in accordance with an example.

FIG. 2 illustrates an example of transferring energy or data between a plurality of wireless transfer coils 210 and 220. FIG. 2 further illustrates that one of the plurality of wireless transfer coils 210 can be a transmitting coil 210 and another one of the plurality of wireless transfer coils 220 can be a receiving coil 220. In one embodiment, energy and/or data can be transferred from the transmitting coil 210 to the receiving coil 220 by coupling the transmitting coil 210 with the receiving coil 220 to enable the energy or data to be transferred over a gap or distance. In one example, wireless energy can be transferred by generating a magnetic field 230 (such as an electromagnetic field) at the transmitting coil 210 and positioning the receiving coil 220 within the magnetic field 230 to induce a current at the receiving coil 220. The process of inducing a current at the receiving coil is referred to as coupling the receiving coil 220 to the transmitting coil 210. In one embodiment, the wireless transfer coil coupling for wireless energy or data transfer can be a magnetic induction coupling. In another embodiment, the wireless transfer coil coupling for wireless energy transfer can be a magnetic resonant coupling.

In one embodiment, the transmitting coil 210 can be a transmitting induction coil and the receiving coil 220 can be a receiving induction coil. The wireless transfer station can use a magnetic field to transfer energy between the transmitting coil 210 coupled to a first object (such as a wireless transfer station) and a receiving coil 220 of a second object (such as another wireless transfer station) without any direct contact between the transmitting coil 210 and the receiving coil 220, e.g. inductive coupling.

In one embodiment, inductive coupling can occur when the transmitting coil 210 creates a magnetic field 230 (such as an alternating electromagnetic field) using an energy source, such as an alternating current (AC) energy outlet or a direct current (DC) battery. A current can be induced at the receiving coil 220 using the magnetic field when the receiving coil 220 is located within the magnetic field 230.

In one example, when the transmitting coil 210 and the receiving coil 220 are within a threshold proximity distance, the transmitting coil 210 and the receiving coil 220 can couple to form an electric transformer. In one embodiment, current from the receiving coil 220 can be transferred to a battery or an electronic device. In another embodiment, the current can be stored in one or more energy sources of the wireless transfer station, such as a battery. In another embodiment, the current can be transferred to a device coupled to the wireless transfer station. In one embodiment, an impedance of one or more transmitting coils 210 can be substantially matched with an impedance of one or more receiving coils 220.

In one embodiment, the transmitting coil 210 can be a transmitting resonant coil and the receiving coil 220 can be a receiving resonant coil. A wireless resonant transfer can be a resonant transmission of energy or data between at least one transmitting coil 210 and at least one receiving coil 220. In another embodiment, at least one transmitting coil 210 and at least one receiving coil 220 can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil 210 can be configured to oscillate current at the resonant frequency of the coils to transfer energy and/or data. The oscillating current of the transmitting coil 210 can generate an oscillating magnetic field at the selected resonant frequency of the receiving coil. When the receiving coil 220 is positioned adjacent to the oscillating magnetic field and constructed to operate at the same frequency or substantially the same frequency as the transmitting coil 210, the receiving coil 220 can receive energy and/or data from the oscillating magnetic field.

In another embodiment, an impedance of one or more transmitting coils 210 can be substantially matched with an impedance of one or more receiving coils 220 for energy and/or data transfer. In another embodiment, the transmitting coil and the receiving coil can be positioned such that the receiving coil is within the near field of the magnetic field of the transmitting coil. The near field can be based within the Fraunhofer region, which can be approximately within ½π times the wavelength of the electromagnetic field.

One advantage of placing the receiving coil within the near field for wireless energy transfer is to reduce an amount of energy that may be radiated or leaked from the wireless transfer coils 210 and 220, e.g. energy not received at the receiving coil 220. In one embodiment, energy in a magnetic field falls off as the inverse squared of a distance ($1/d^2$) between the transmitting coil 210 and the receiving coil 220 within the near field. In one example, magnetic resonant coupling can be used to transfer energy at relatively high energy levels between the transmitting coil 210 and the receiving coil 220 and to minimize or reduce energy leaking away from the wireless transfer coils 210 and 220.

Another advantage of using a near field or a non-radiating field for wireless energy transfer can be that the near field or the non-radiating field can be used in areas adjacent to biological material, such as humans or other biological entities, with minimal or no effects to the biological material from the wireless energy transfer. In another embodiment, a wireless transfer station, such as in FIG. 1, can use a radio frequency (RF) signal, ultrasound, and/or laser beams to wirelessly transfer energy and/or data between a transmitting device and a receiving device.

Figure 3A:
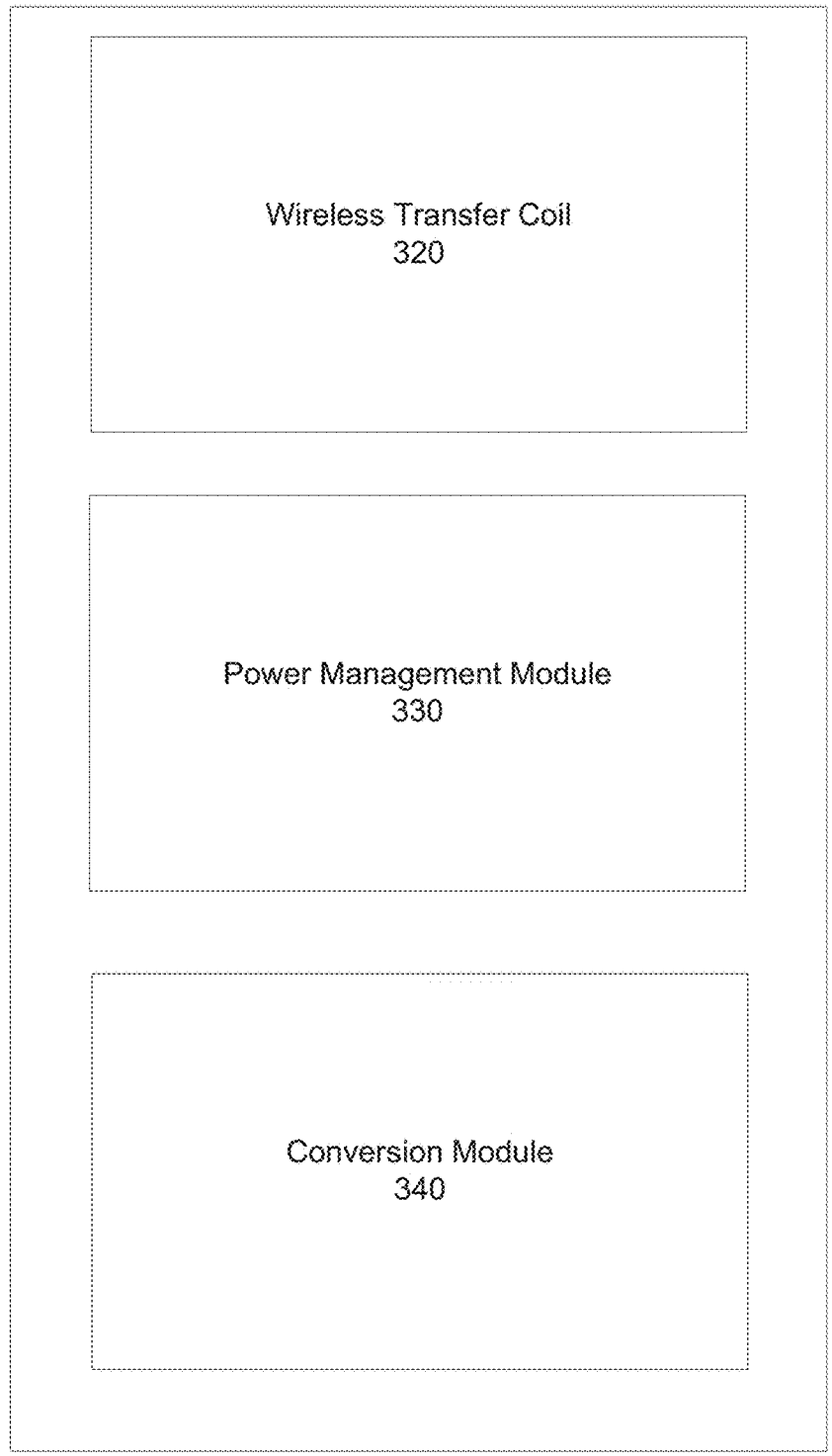
FIG. 3a depicts a wireless transfer station in accordance with an example.

FIG. 3a shows a wireless transfer station 310 that can include: a wireless transfer coil 320, a power management module 330, and a conversion module 340. In one embodiment, the wireless transfer coil 320 can be used for resonance coupling and/or induction coupling. In one example, the conversion module 340 can be coupled to the wireless transfer coil 320 and used to switch the wireless transfer coil 320 from a resonance mode (i.e. transferring wireless energy and/or data using magnetic resonance coupling) to an induction mode (i.e. transferring wireless energy and/or data using magnetic induction coupling), or vice versa.

In one embodiment, the wireless transfer coil 320 of the wireless transfer station 310 can be used for transmitting wireless energy and/or receiving wireless energy. In one example, the conversion module 340 can be coupled to the wireless transfer coil 320 and used to switch the wireless transfer coil 320 from a receiving mode (i.e. receiving wireless energy and/or data) to a transmitting mode (i.e. transmitting wireless energy and/or data), or vice versa.

In one embodiment, when the conversion module 340 of the wireless transfer station 310 is in the transmitting mode, the conversion module 340 or the power management module 330 can convert energy received from an energy source (such as a power outlet or a battery) at a selected voltage into a high frequency alternating current and transmit the high frequency alternating current to a wireless transfer coil of another wireless transfer station. The high frequency alternating current can flow through one or more loops of the wireless transfer coil 320 and create a varying magnetic field that can induce a current in the other wireless transfer coil. In another embodiment, when the conversion module 340 is switched to the receiving mode, a varying magnetic field from another wireless transfer station can induce an alternating current flowing through the one or more loops of the wireless transfer coil 320. The current flowing through the one or more loops can be converted into a direct current (DC) by the conversion module 340 or the power management module 330 and directed to a battery coupled to the wireless transfer station 310 or a device that is electrically coupled to the wireless transfer station 310.

In one embodiment, each wireless transfer coil 320 of a wireless transfer station 310 can be coupled to a separate conversion module 340. In another embodiment, one or more conversion modules 340 can be coupled to one or more selected groups of wireless transfer coils 320. One advantage of using a conversion module 340 for switching a wireless transfer coil 320 between transmitting mode and receiving mode can be to reduce a complexity of design and/or size of a wireless transfer station 310 by reducing a number of wireless transfer coils 320 used to transmit and/or receive wireless energy. Another advantage of using a conversion module 340 for switching a wireless transfer coil between a transmitting mode and receiving mode is to provide a dual functionality to a wireless transfer station of both transmitting and receiving wireless energy.

Figure 3B:
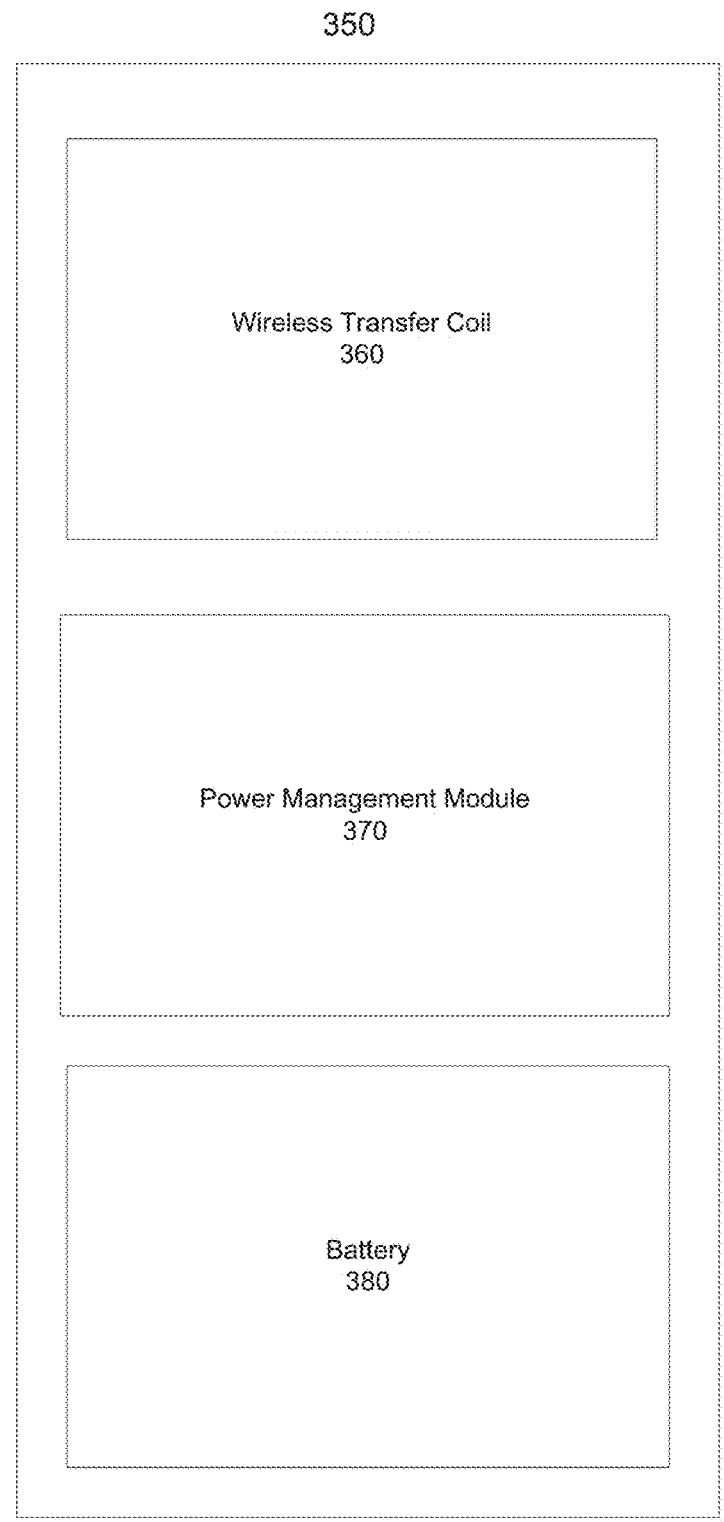
FIG. 3b depicts another wireless transfer station in accordance with an example.

FIG. 3b illustrates a wireless transfer station 350. FIG. 3b further illustrates that the wireless transfer station 350 can include: a wireless transfer coil 360; a power management module 370; and a battery 380. The battery 380 can comprise a plurality of batteries, such as rechargeable batteries. In one example, the power management module 370 can convert energy received using the wireless transfer coil 360 from an energy source, such as another wireless transfer station or an alternating current (AC) energy outlet, to a selected current level at a selected voltage level to provide a selected wattage level. In one embodiment, the power management module can transfer the converted energy to the battery 380 to store the energy.

Figure 3C:
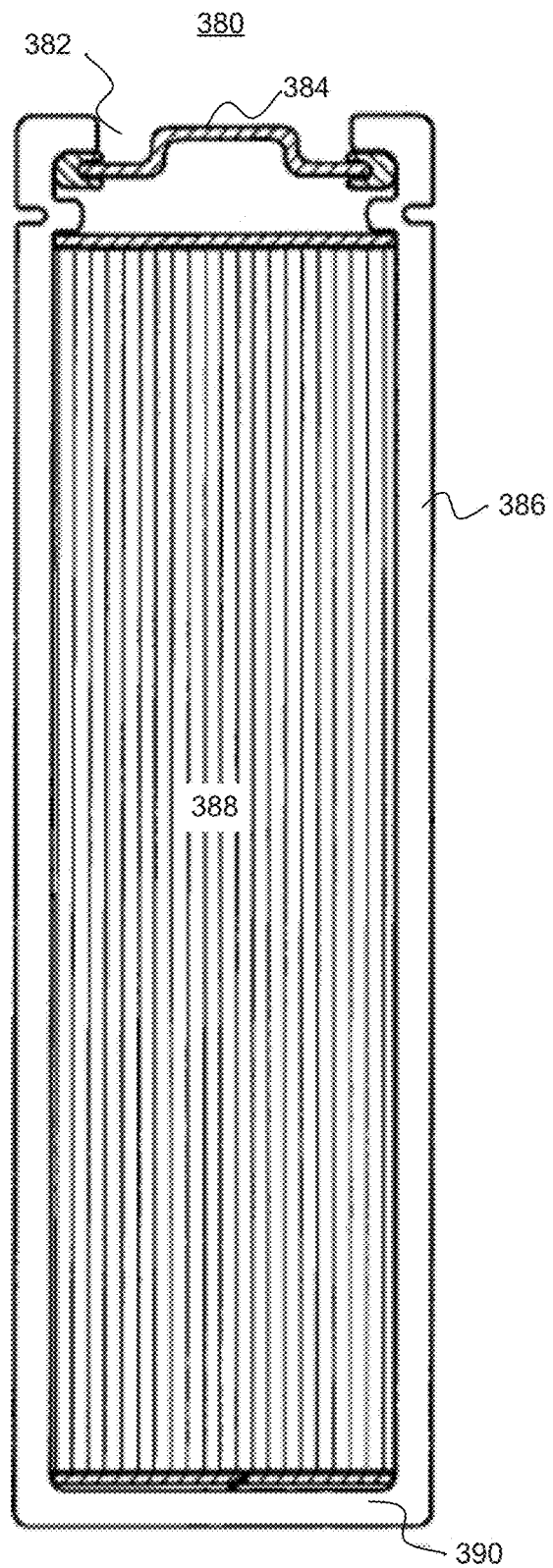
FIG. 3c depicts a cross-sectional view of a battery in accordance with an example.

FIG. 3c shows a cross-sectional view of a battery 380, for example a lithium ion battery utilizing an 18650 battery form-factor. The battery 380 can include: a case 386, such as a cylindrical case; one or more electrodes 388, and a cap 384. In one embodiment, the case 386 can be made of a metal, such as nickel-plated steel, that can be non-reactive with battery materials, such as an electrolyte or the one or more electrodes 388. In one embodiment, a bottom surface 390 of the case 386 can be seamlessly integrated with the remainder of the case 386. In one embodiment, a top end 382 of the case 386 can be open ended. In another embodiment, the cap 384 can be located at the top end 382 of the case 386. In another embodiment, the top end 382 can be a positive electrical terminal of the battery 380 and the bottom end 390 can be a negative electrical terminal. In one example, the positive electrical terminal and the negative electrical terminal of the battery 380 can be connected to a wireless transfer station to provide energy to the wireless transfer station. In another embodiment, a plurality of batteries can be connected in series and/or in parallel. In one embodiment, the battery 380 can be connected to a power management module, such as the power management modules in FIGS. 3a and 3b.

Figure 4:
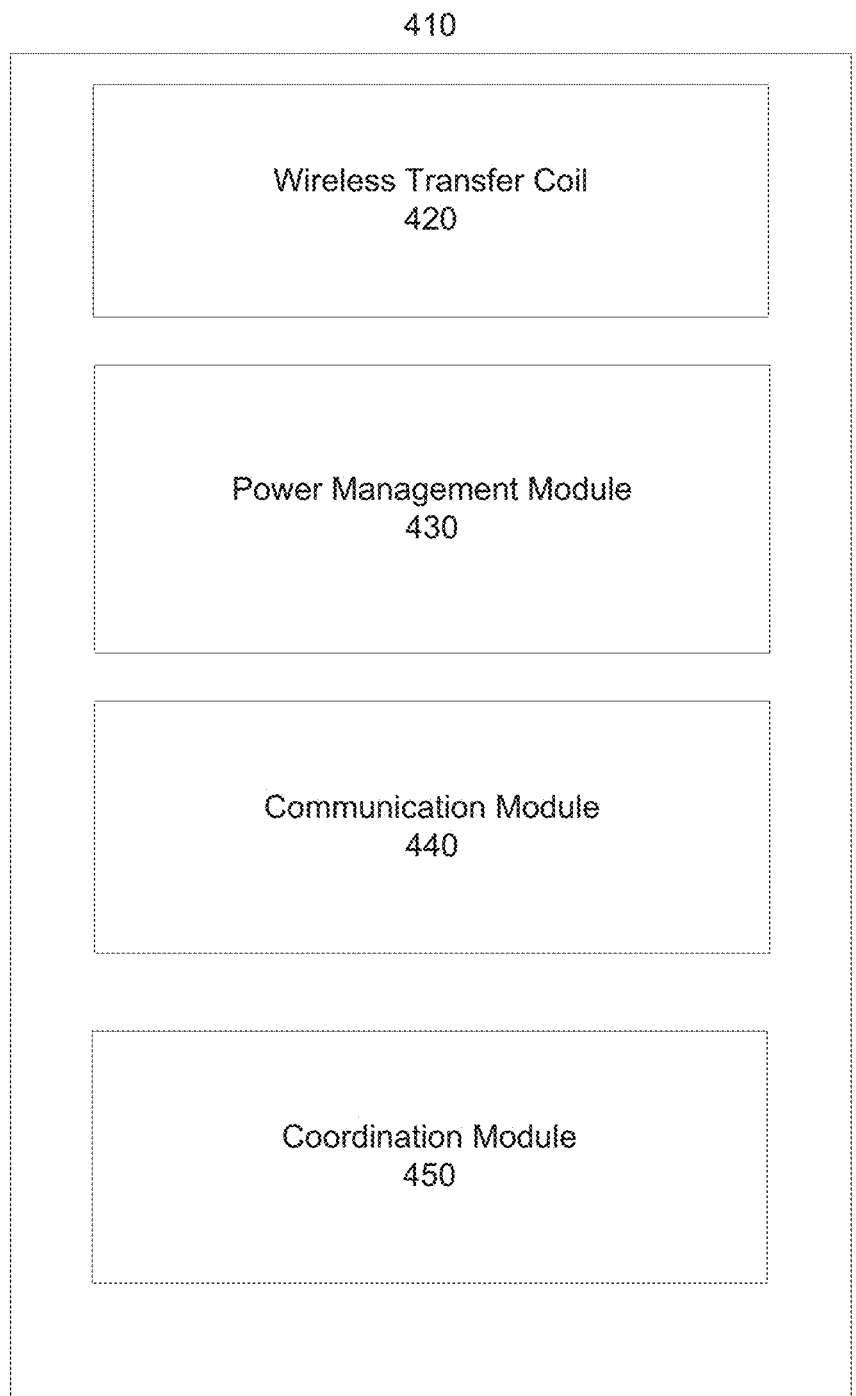
FIG. 4 depicts a wireless transfer station in accordance with an example.

FIG. 4 shows a wireless transfer station 410 that can include: a wireless transfer coil 420, a power management module 430, a communications module 440, and/or a coordination module 450. In one embodiment, the wireless transfer station 410 can communicate with one or more other wireless transfer stations or one or more devices using the communication module 440.

In one embodiment, the communication module 440 of the wireless transfer station 410 can use a communications network to communicate the data to a device and/or another wireless transfer station. In another embodiment, the communications network can be a cellular network that may be a 3GPP LTE Rel. 8, 9, 10, 11,or 12 or IEEE 802.16p, 802.16n, 802.16m-2011, 802.16h-2010, 802.16j-2009, 802.16-2009.In another embodiment, communications network can be a wireless network (such as a wireless fidelity network (Wi-Fi)) that may follow a standard such as the Institute of Electronics and Electrical Engineers (IEEE) 802.11-2012,IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a ZigBee connection such as IEEE 802.15.4-2003 (ZigBee 2003), IEEE 802.15.4-2006 (ZigBee 2006), IEEE 802.15.4-2007 (ZigBee Pro).

In one embodiment, the wireless transfer station 410 can transfer energy to one or more other wireless transfer stations, receive energy from one or more other wireless transfer stations, and/or communicate data or information with one or more other wireless transfer stations. In another embodiment, the coordination module 450 of the wireless transfer station 410 can coordinate when energy is transferred between wireless transfer stations and/or when data is communicated between wireless transfer stations. In another embodiment, the coordination module 450 can use the communications module 440 to communicate with one or more other wireless transfer stations to coordinate energy and/or data transfer between the wireless transfer station 410 and the one or more other wireless transfer stations.

One advantage of transferring energy and/or data using a wireless transfer station 410 is to provide a single connection point between the wireless transfer station 410 and other wireless transfer stations and/or other devices. Another advantage of transferring energy and/or data using the wireless transfer station 410 can be to enable a single step for both transferring energy between the wireless transfer station 410 and other wireless transfer stations and communicating or synchronizing data communicated between the wireless transfer station 410 and other wireless transfer stations. In one example, when a first wireless transfer station (such as a wireless transfer station integrated into a medical cart) is located adjacent to a second wireless transfer station (such as a wireless transfer station integrated into a plate mounted to a wall or a floor mat), the first wireless transfer station can both receive energy from the second wireless transfer station and synchronize information with the second wireless transfer station.

In one embodiment, the coordination module 450 can communicate with a conversion module, as in FIG. 3a, to coordinate when one or more wireless transfer coils 420 of the wireless transfer station 410 can transmit and/or receive wireless energy and/or data. In one example, the coordination module 450 communicates with a conversion module, as in FIG. 3a, to coordinate transmitting and/or receiving wireless energy and/or data by coordinating when one or more wireless transfer coils 420 are in a transmitting mode or a receiving mode, as discussed in the preceding paragraphs.

Figure 5A:
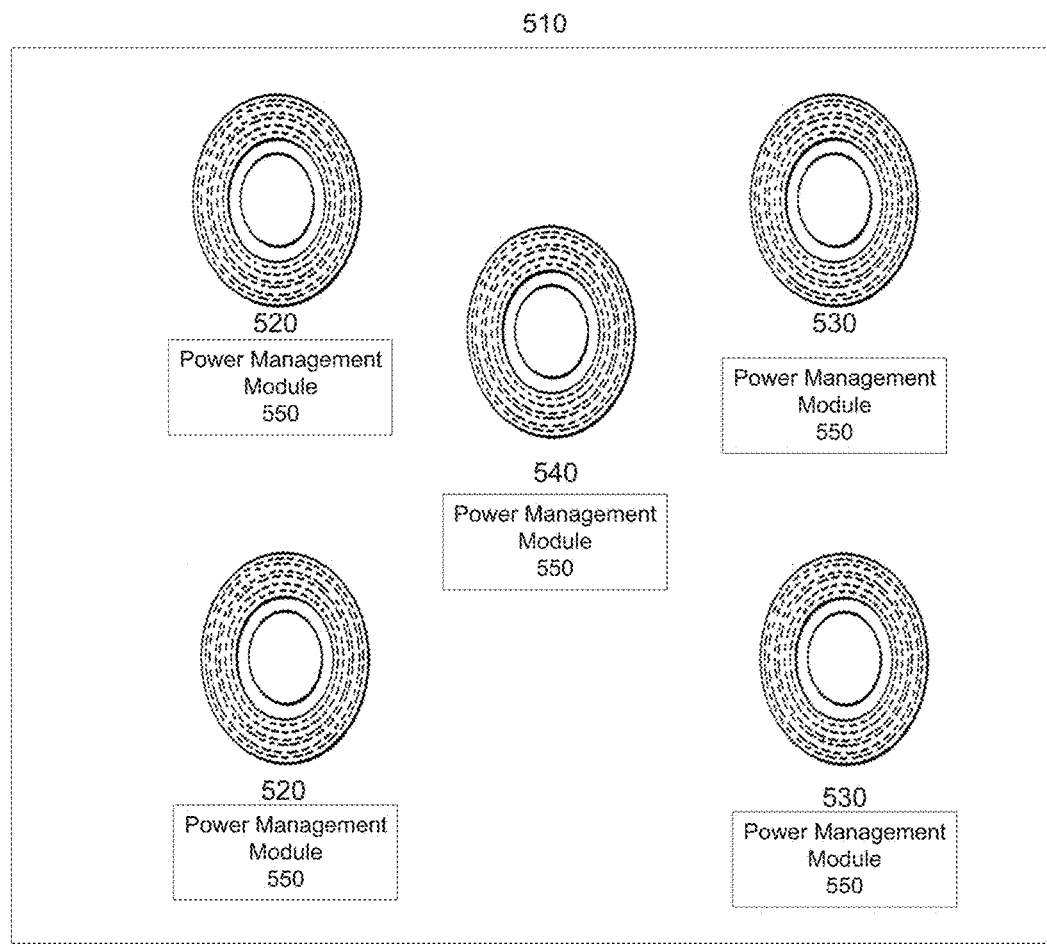
FIG. 5a depicts a wireless transfer station that includes one or more resonant wireless transfer coils and/or one or more induction wireless transfer coils in accordance with an example.

FIG. 5a shows a wireless transfer station 510 that includes one or more resonant wireless transfer coils 520 and/or one or more induction wireless transfer coils 530. In one example, the wireless transfer station 510 can have a resonant wireless transfer coil 520 and can transfer energy to a resonant wireless transfer coil of a first wireless transfer station and can have an induction wireless transfer coil 530 and can transfer energy to an induction wireless transfer coil of a second wireless transfer station. One advantage of the wireless transfer station having both resonant wireless transfer coils 520 and induction wireless transfer coils 530 can be to provide energy and/or data to wireless transfer stations and/or devices with only one of the resonant wireless transfer coils or the induction wireless transfer coils, thereby enabling more devices to transfer energy to the wireless transfer station.

In one embodiment, a device or another wireless transfer station can include one or more resonant wireless transfer coils and/or one or more induction wireless transfer coils. In one embodiment, the device or the other wireless transfer station receiving energy from the wireless transfer station 510 can select whether to receive wireless energy from the one or more resonant wireless transfer coils 520 or the one or more induction wireless transfer coils 530 of the wireless transfer station 510. In another embodiment, the wireless transfer station 510 can be configured to select whether to transmit wireless energy using the one or more resonant wireless transfer coils 520 or the one or more induction wireless transfer coils 530. In one example, a resonant transmitting coil and a resonant receiving coil pair can have a higher energy transfer efficiency than an induction transmitting coil and an induction receiving coil pair. In this example, when the device or the other wireless transfer station includes a resonant receiving coil, the other wireless transfer station and/or the device or the wireless transfer station 510 can be configured to use one or more resonant wireless transfer coils to perform an energy transfer.

In one embodiment, the one or more resonant wireless transfer coils 520 and/or the one or more induction wireless transfer coils 530 can be transmitting coils and/or receiving coils. In another embodiment, the wireless transfer station 510 can include one or more repeater coils 540. In one example, the repeater coil 540 can enhance wirelessly transmitted energy of a transmitting coil, e.g. providing additional transmission energy. In another example, the repeater coil 540 can receive the wireless energy from a transmitting coil and relay or retransmit the received energy to another repeater coil 540 or to a receiving coil. The repeater coils can be configured as inductive repeater coils or resonant repeater coils, and associated with transmit coils and receive coils of the same kind.

In one embodiment, the one or more resonant wireless transfer coils 520, the one or more induction wireless transfer coils 530, and/or the repeater coil 540 can include a power management module 550 configured to covert energy from an energy source to a varying magnetic field. In another embodiment, the one or more resonant wireless transfer coils 520, the one or more induction wireless transfer coils 530, and/or the repeater coil 540 can be coupled to a power management module 550 configured to convert a magnetic field into energy, such as energy at a selected current level, a voltage level, a wattage level, and/or an amperage level, and transfer the energy to a battery of the wireless transfer station 510 or a device coupled to the wireless transfer station 510.

Figure 5B:
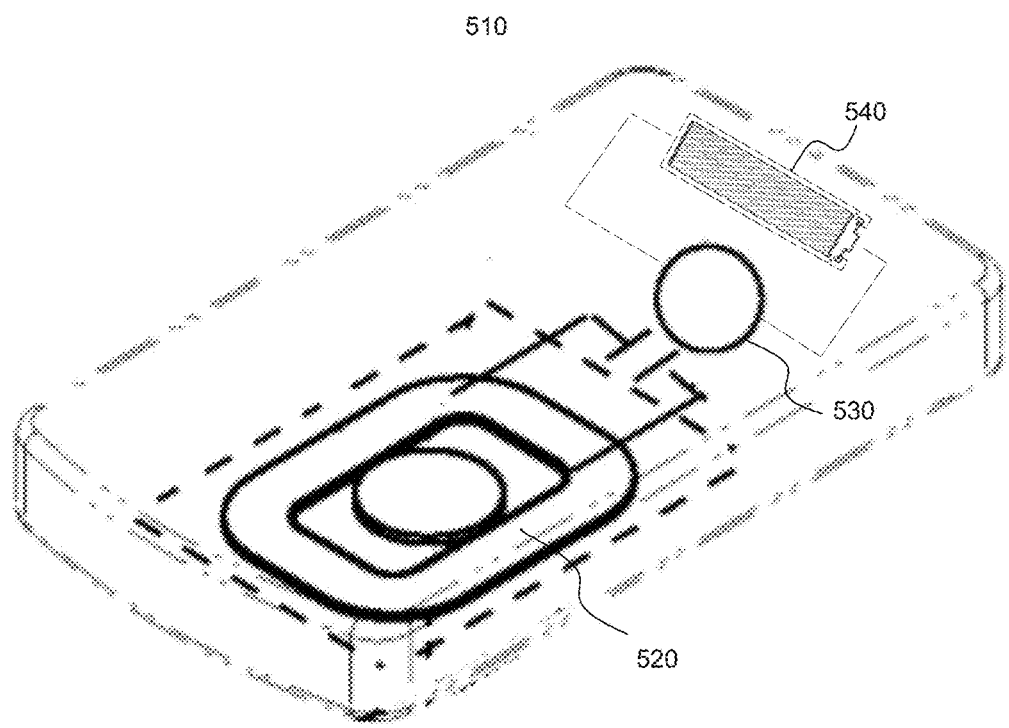
FIG. 5b depicts a wireless transfer station in accordance with an example.

FIG. 5b illustrates one exemplary embodiment of the wireless transfer station 510. In one embodiment, the wireless transfer station 510 can be a stand-alone device used to transfer wireless energy to other devices. In another embodiment, the wireless transfer station 510 can include a wireless transfer coil 520 and a power management module 530. In another embodiment, the wireless transfer station 510 can direct energy received at the wireless transfer coil 520 using the power management module 530 to a device coupled to the wireless transfer station 510.

In another embodiment, the wireless transfer station 510 can transfer the energy received at the wireless transfer coil 520 to the coupled device using physical electrical contacts. In another embodiment, the wireless transfer station 510 can transfer the energy to the coupled device using the wireless transfer coil 520. In one embodiment, the wireless transfer station 510 can store received energy at a battery 540.

Figure 5C:
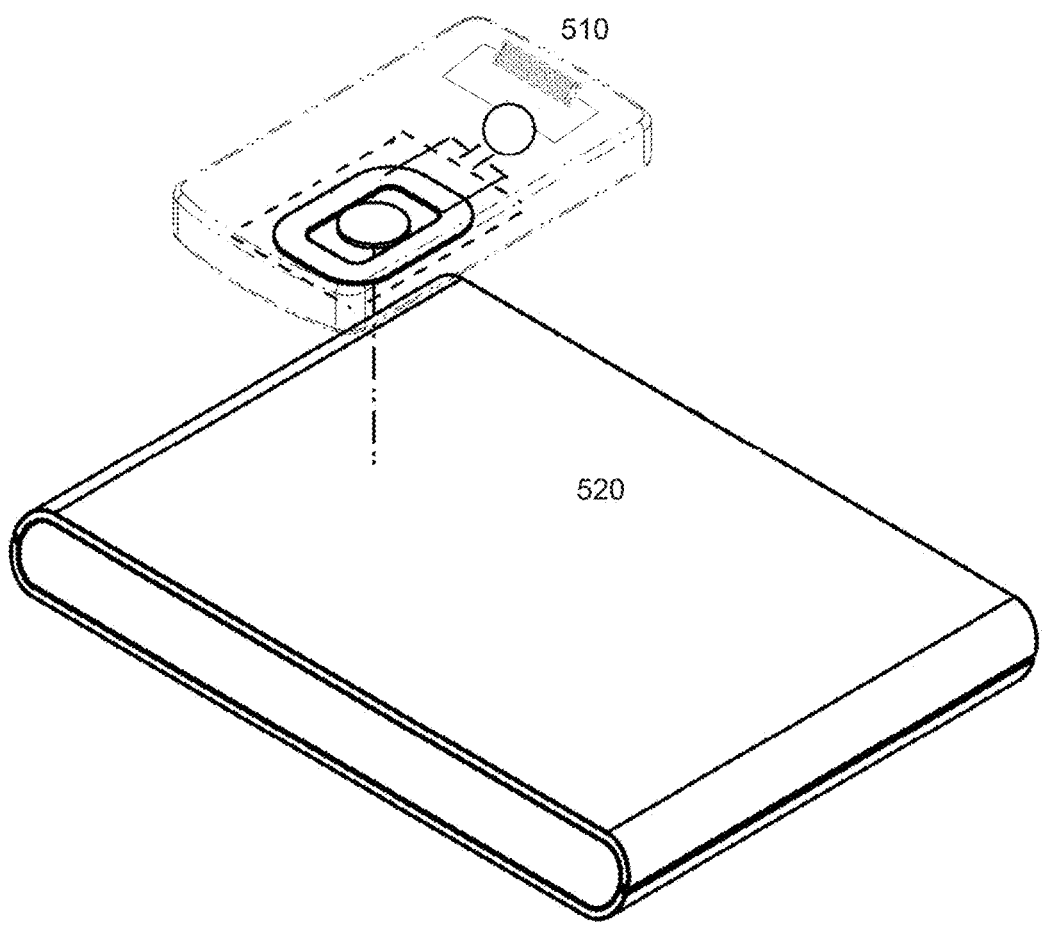
FIG. 5c depicts a wireless transfer station integrated into an object in accordance with an example.
Figure 5D:
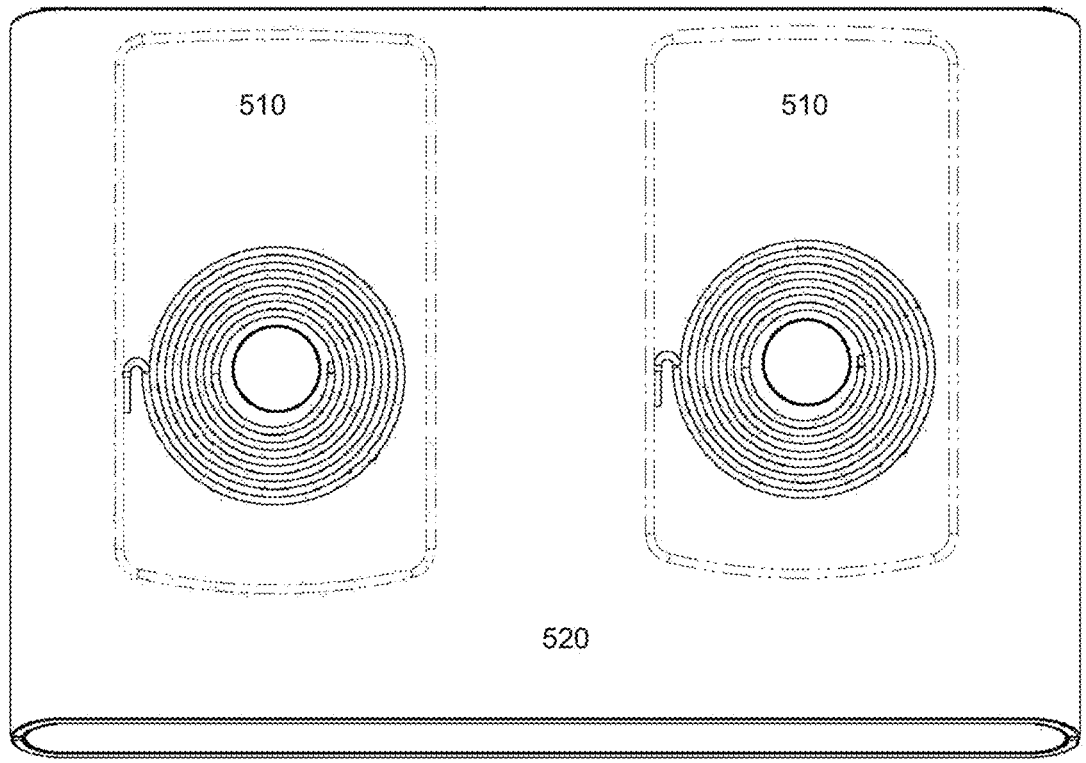
FIG. 5d depicts a plurality of wireless transfer stations integrated into an object in accordance with an example.

FIG. 5c illustrates one exemplary embodiment of the wireless transfer station 510 integrated into an object 520. In one embodiment, the object 520 that the wireless transfer station 510 can be integrated into can be an electronic device, such as a medical device or a wireless energy battery pack. In one example, the wireless transfer station 510 can be integrated into a medical infusion pump and provide energy to the medical infusion pump. In another embodiment, the object 520 can be integrated into a medical cart (such as a work surface of the medical cart), a floor mat, a floor surface, a plate mounted to a wall, a wall surface, chair railing, a room railing, a ceiling tile, a ceiling surface, and so forth. FIG. 5d illustrates that a plurality of wireless transfer stations 510 can be integrated into an object 520. FIG. 5d is the same as FIG. 5c in all other aspects.

Figure 6:
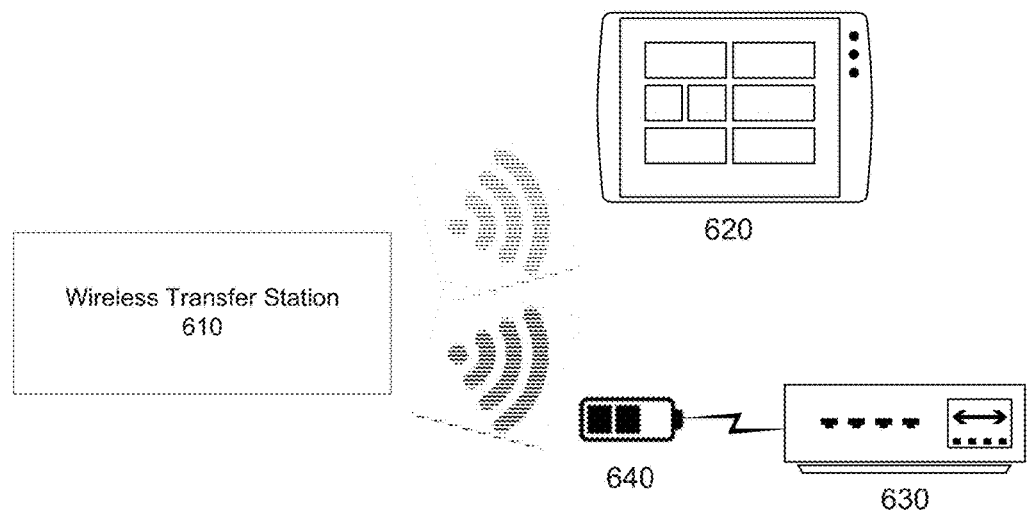
FIG. 6 depicts a wireless transfer station that can provide energy to one or more non-wire powered electronic devices and/or one or more recharge batteries coupled to a device in accordance with an example.

FIG. 6 shows a wireless transfer station 610 that can provide energy to one or more non-wire powered electronic devices 620 and/or one or more rechargeable batteries 640 coupled to a device 630. In another embodiment, the wireless transfer station 610 can provide energy to different types of non-wire powered electronic devices, such as a monitoring device, a computing device, a medical device, and so forth. In one example, the wireless transfer station 610 can provide a unified energy source for the devices 620 and 630 and/or the one or more rechargeable batteries 640 coupled to the device 630. In one embodiment, a unified energy source can be a power source that can provide power to a device, a wireless transfer station, and/or a battery without using different power connectors to provide the power to the device, the wireless transfer station, and/or the battery. In one embodiment, the wireless transfer stations can include an integrated wireless energy coil and a physical electrical energy connection terminal. In another embodiment, the wireless transfer station 610 can transfer energy via an electrical energy connection terminal and/or an integrated wireless transfer coil.

Figure 7A:
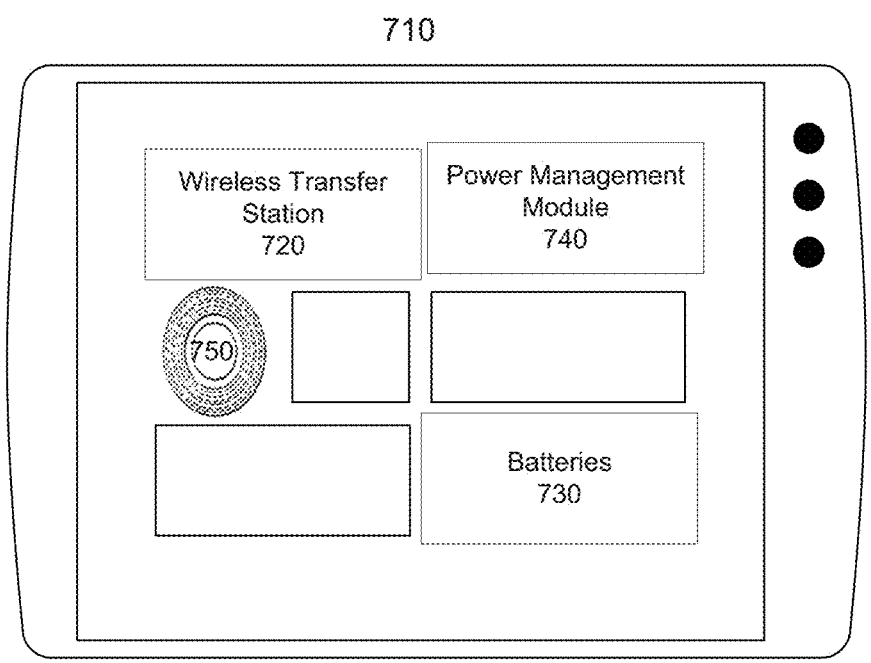
FIG. 7a depicts a device with a wireless transfer station coupled to a device or integrated into the device in accordance with an example.

FIG. 7a shows a device 710 with a wireless transfer station 720 coupled to the device 710 or integrated into the device 710. In one embodiment, the wireless transfer station 720 can be configured to provide energy to batteries 730 of the device 710 and the batteries 730 can provide energy to the device 710. In another embodiment, the wireless transfer station 720 can be configured to provide energy directly to the device 710, e.g. without using batteries. In one example, a power management module 740 can provide energy directly to the device 710 by receiving energy at a wireless transfer coil 750 of the wireless transfer station 710 from a wireless transfer coil of another wireless transfer station and direct the energy via the power management module 740 to the device 710 and/or the batteries 730.

Figure 7B:
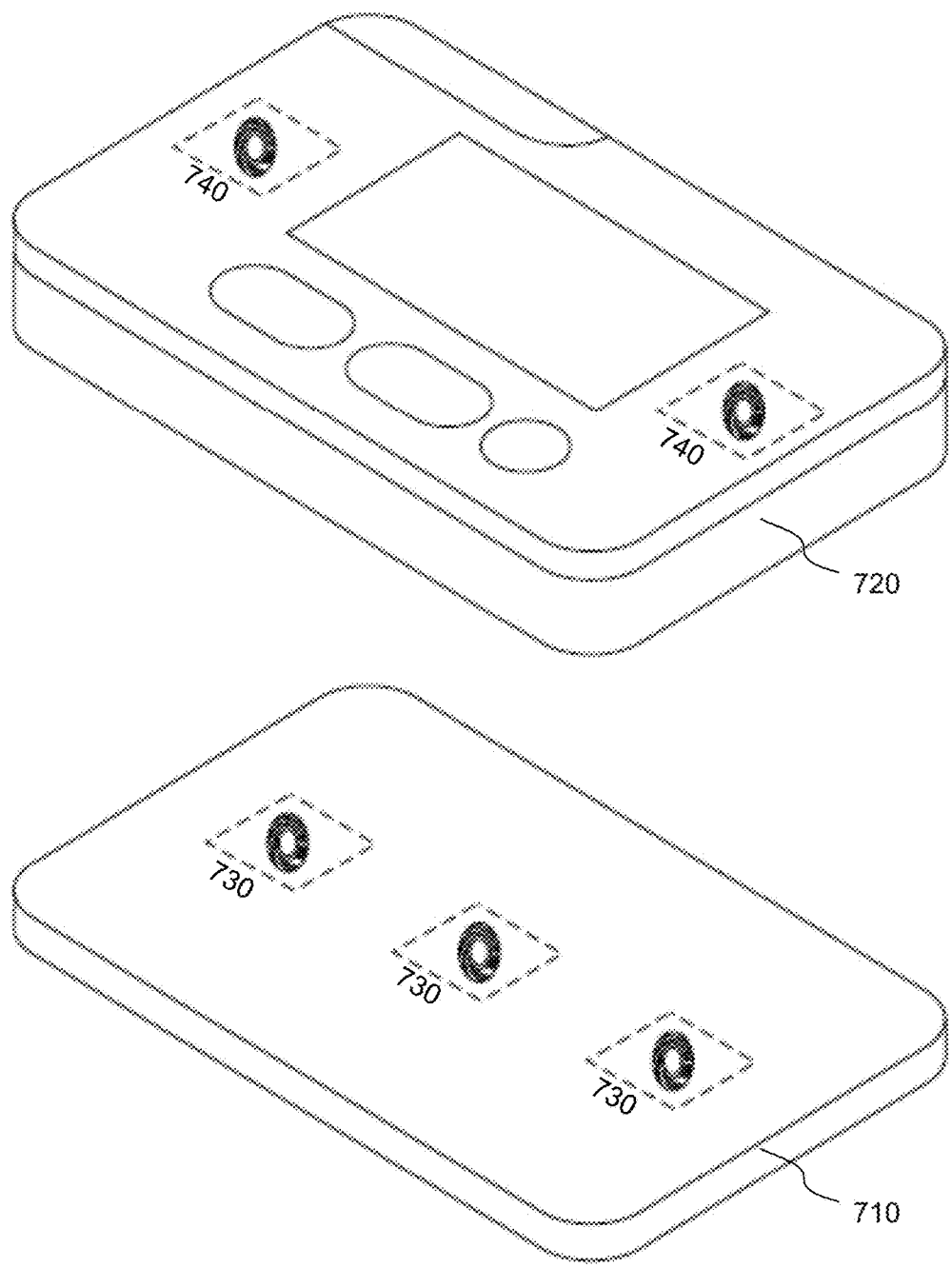
FIG. 7b depicts a wireless transfer station with a plurality of wireless transfer coils configured to transfer energy and/or data to an electronic device in accordance with an example.

FIG. 7b illustrates a wireless transfer station 710 with a plurality of wireless transfer coils 730 configured to transfer energy and/or data to an electronic device 720, such as a medical device. The medical device can include one or more integrated wireless transfer stations 740. In one embodiment, the electronic device 720 can be located adjacent to the wireless transfer station 710. For example, a bottom surface of the electronic device 720 can abut a top surface of the wireless transfer station 710.

In one embodiment, the wireless transfer station or one or more components of the wireless transfer station can be incorporated into a device. The device can be: a wheeled medical cart; a platform coupled the wheeled medical cart; a platform integrated into the wheeled medical cart; and/or a device coupled the wheeled medical cart.

Figure 8C:
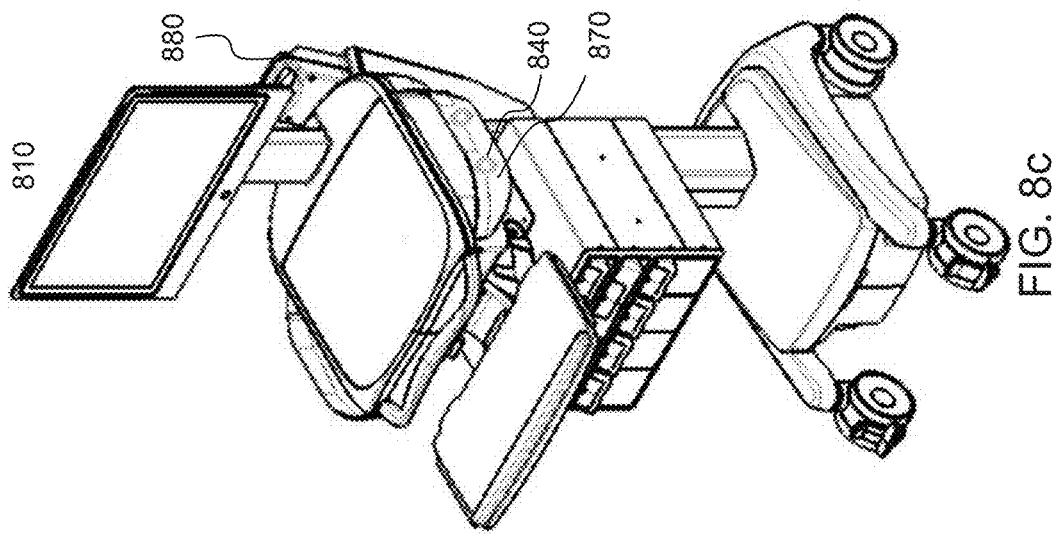
FIG. 8c depicts a wheeled medical cart with one or more wireless transfer stations integrated into a device holder of the wheeled medical cart in accordance with an example.
Figure 8B:
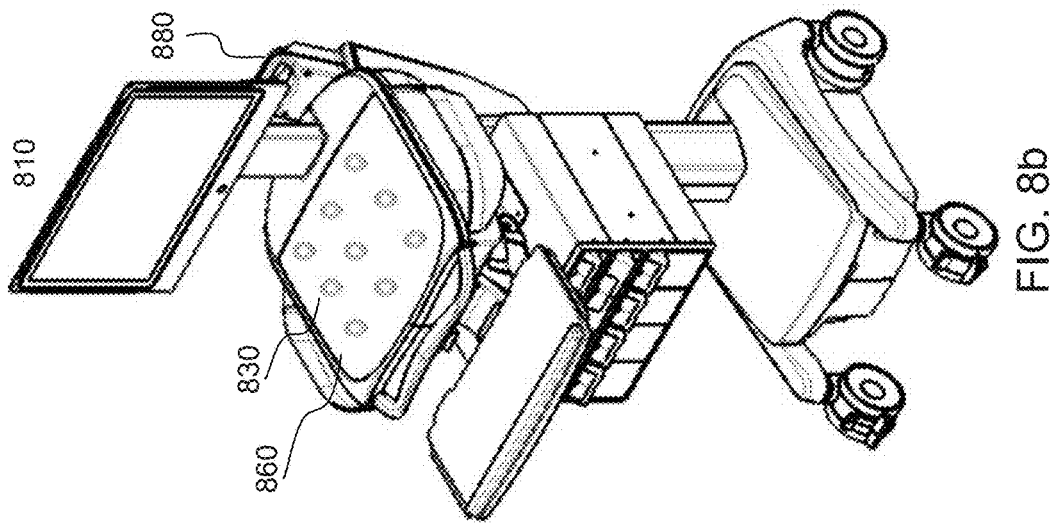
FIG. 8b depicts a wheeled medical cart with a plurality of wireless transfer stations integrated into a work surface of the wheeled medical cart in accordance with an example.
Figure 8A:
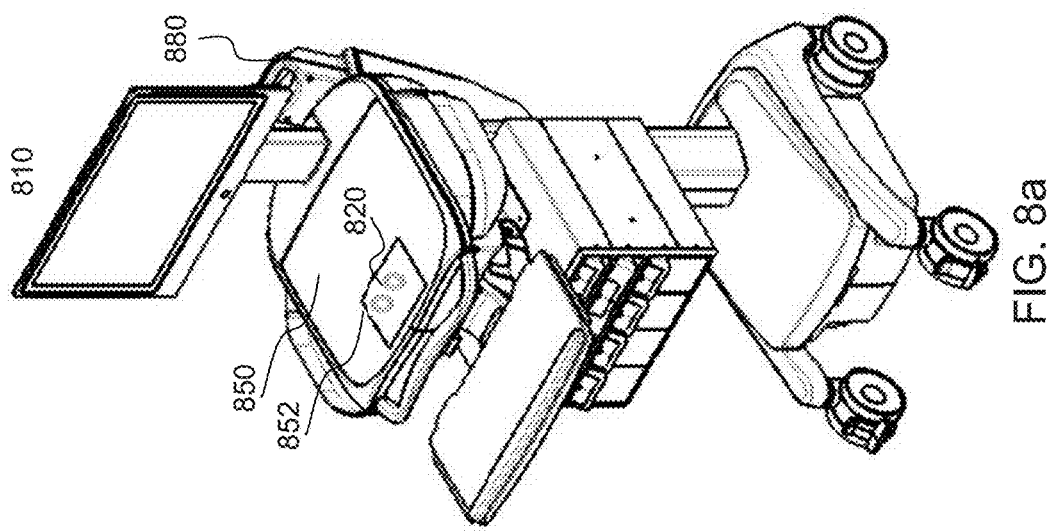
FIG. 8a depicts a wheeled medical cart with a plurality of wireless transfer stations integrated into a selected area of a work surface of the wheeled medical cart in accordance with an example.

FIGS. 8a, 8b, and 8c show a wheeled medical cart 810 with different configurations of integrated wireless transfer stations 820, 830, and 840, respectively. FIG. 8a shows a wheeled medical cart 810 with a plurality of wireless transfer stations 820 integrated into a selected area 852 of a work surface 850 of the wheeled medical cart 810. FIG. 8b shows a wheeled medical cart 810 with a plurality of wireless transfer stations 830 integrated into a work surface 860 of the wheeled medical cart 810. The wheeled medical cart 810 of FIG. 8b is the same as the wheeled medical cart 810 in FIG. 8a in all other regards. FIG. 8c shows a wheeled medical cart 810 with one or more of wireless transfer stations 840 integrated into a device holder 870 of the wheeled medical cart 810. The wheeled medical cart 810 of FIG. 8c is the same as the wheeled medical carts 810 in FIGS. 8a and 8b in all other regards.

In one embodiment, the wheeled medical cart 810 can have one or more attached work surfaces 850 or 860. In one example, the one or more work surfaces 850 or 860 and/or device holder 870 of the wheeled medical cart can include one or more integrated or coupled wireless transfer coils, such as one or more transmitting coils, one or more repeater coils, and/or one or more receiving coils. In another embodiment, the one or more work surfaces 850 or 860 and/or device holder 870 can have one or more selected areas for other devices, such as medical devices and/or mobile devices, to be placed on the one or more work surfaces 850 or 860 and/or device holder 870 and receive wireless energy.

In one embodiment, the device holder 870 can be designed to hold one or more devices at selected alignments to orient the one or more devices to receive energy from one or more of wireless transfer stations 840. In one example, the device holder 870 can be integrated into the wheeled medical cart 810 and the device holder 870 can hold and orient one or more medical devices to receive wireless energy using wireless transfer stations coupled to the medical devices and/or wireless transfer stations integrated into the medical devices.

In one embodiment, the wheeled medical cart 810 can include one or more electrical systems and/or one or more devices coupled to the wheeled medical cart 810. In another embodiment, the wheeled medical cart 810 can use one or more wireless transfer stations 880 to power the one or more electrical systems and/or the one or more devices. In another embodiment, the one or more wireless transfer stations 880 can receive wireless energy while attached to the wheeled medical cart. In another embodiment, the one or more wireless transfer stations 880 can be removed from the wheeled medical cart and can be attached to another wireless transfer station or be located adjacent to the wireless transfer station and receive wireless energy.

Figure 9:
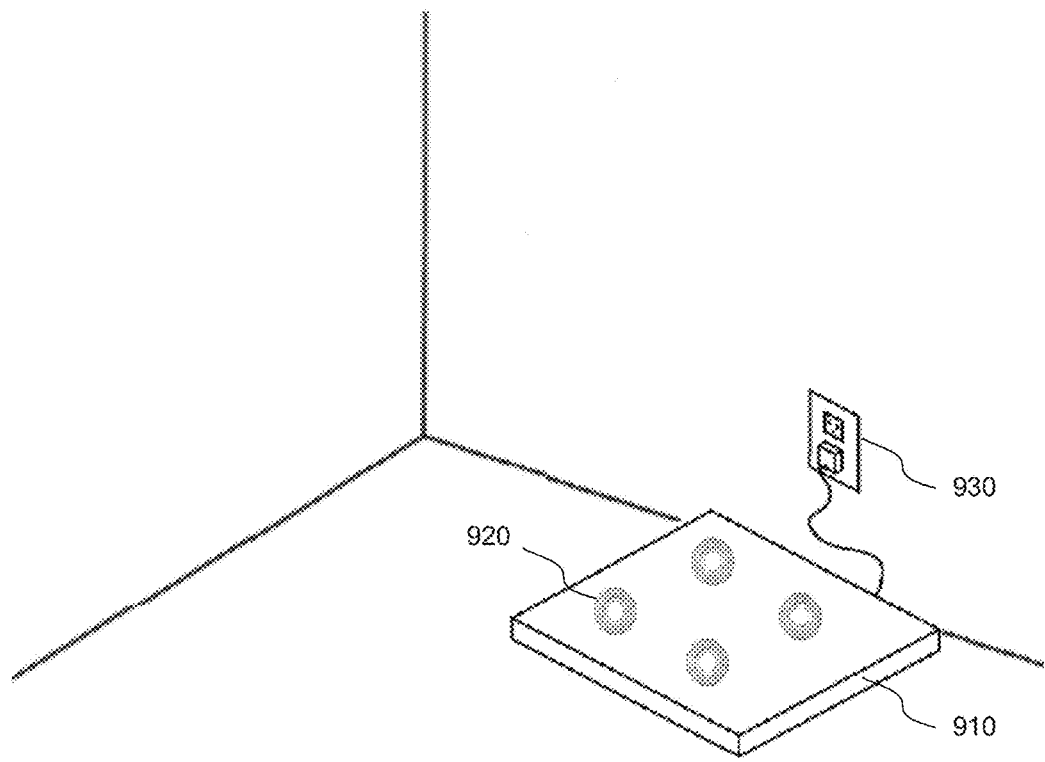
FIG. 9 depicts a floor mat with one or more integrated wireless transfer stations in accordance with an example.

FIG. 9 shows one exemplary embodiment of floor mat 910 with one or more integrated wireless transfer stations 920. In one embodiment, the integrated wireless transfer stations 920 can receive energy and/or data from an outlet 930. In one embodiment, the outlet 930 can be a wall outlet and the integrated wireless transfer stations 920 can receive alternating current (AC) from the outlet 930. In another embodiment, the outlet 930 can be a data outlet, such as an Ethernet outlet, and the integrated wireless transfer stations 920 can receive data from the outlet 930.

In another embodiment, the one or more integrated wireless transfer stations 920 can include one or more wireless transfer coils to transfer energy from the wireless transfer station 920 to another wireless transfer station. In one example, a wireless transfer station coupled to a wheeled medical cart can be moved into a location in proximity or adjacent to the wireless transfer station integrated 920 into the floor mat 910 and receive energy from the one or more wireless transfer stations 920 integrated into the floor mat 910.

Figure 10:
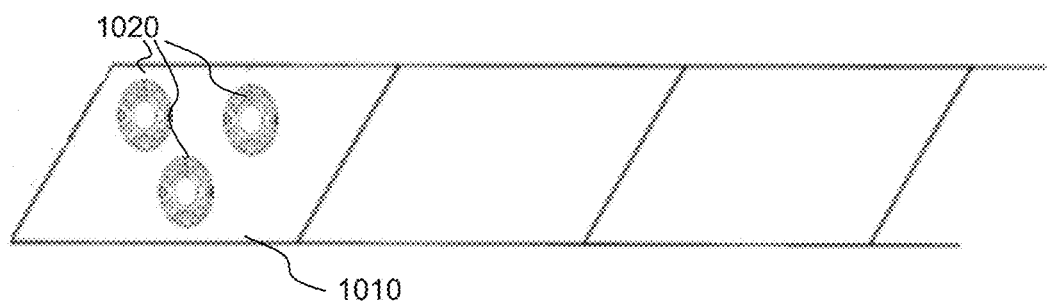
FIG. 10 depicts a flooring surface with one or more integrated wireless transfer stations in accordance with an example.

FIG. 10 shows one exemplary embodiment of a flooring surface 1010 with one or more integrated wireless transfer stations 1020. In another embodiment, the one or more integrated wireless transfer stations 1020 can include one or more wireless transfer coils. In another embodiment, the flooring surface 1010 can be a flooring tile with the one or more integrated wireless transfer stations 1020 integrated into the flooring tile. In another embodiment, the one or more integrated wireless transfer stations 1020 can be coupled to the flooring surface, such as attached to an outer surface of a flooring tile.

Figure 11:
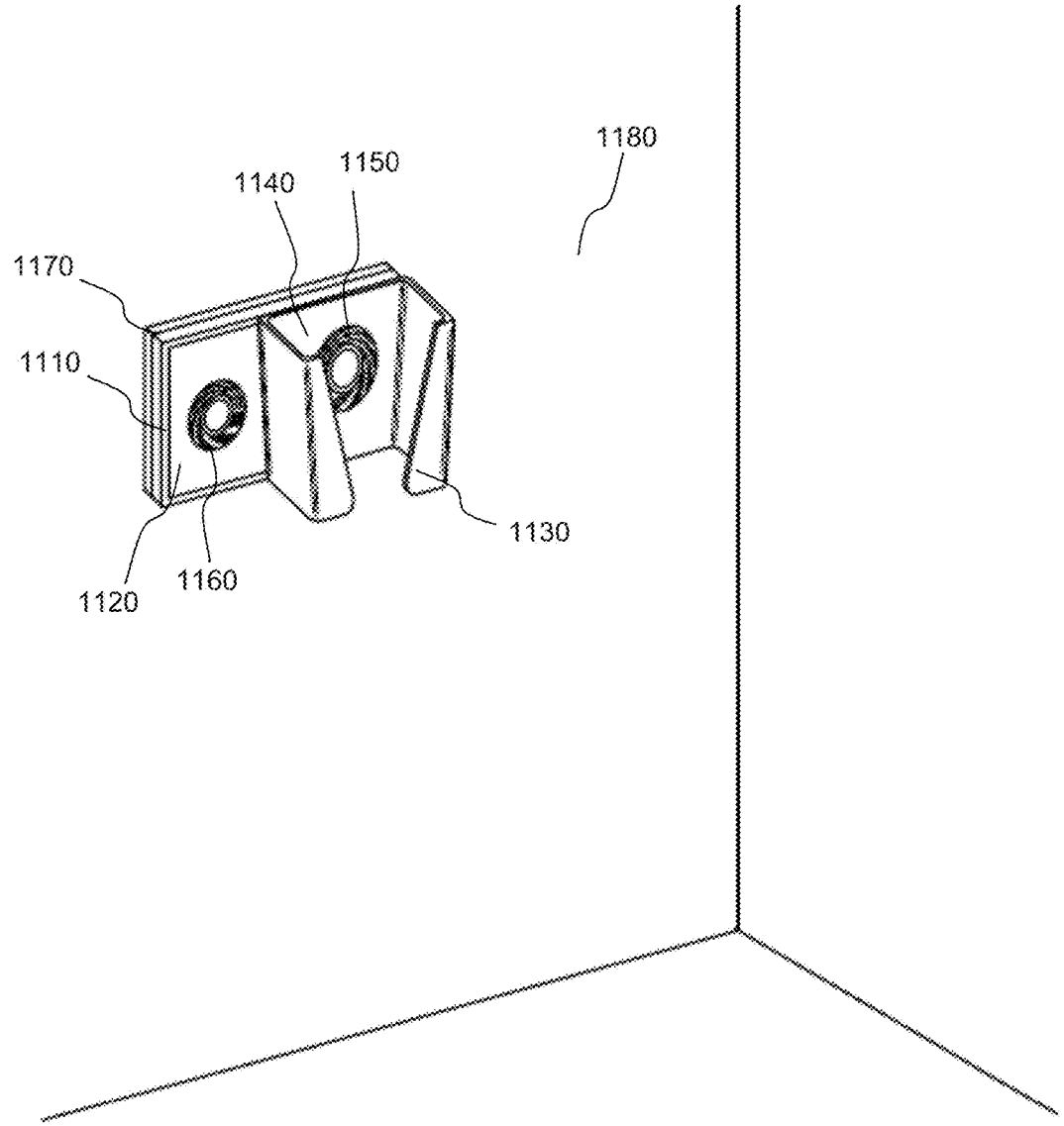
FIG. 11 depicts a plate mounted to a wall with one or more integrated wireless transfer stations in accordance with an example.

FIG. 11 shows one exemplary embodiment of a plate 1110 mounted to a wall 1180 with one or more integrated wireless transfer stations 1120. In another embodiment, the one or more integrated wireless transfer stations 1120 can include one or more wireless transfer coils 1160. In another embodiment, the plate 1110 can be integrated into the wall 1180. In another embodiment, the one or more integrated wireless transfer stations 1120 can be coupled to the wall 1180, such as attached to an inner surface of the wall 1180. In another embodiment, a receptacle 1130 can be attached to the plate 1110. In another embodiment, the receptacle 1130 can receive a device, such as a medical device, or another wireless transfer station. In another embodiment, one or more wireless transfer stations 1140 can be coupled to the receptacle 1130 and the one or more wireless transfer stations 1140 can be used to transfer energy and/or data with the device or the other wireless transfer station, such as by using a wireless transfer coil 1150.

In another embodiment, a plate 1110 can be attached to a mounting plate 1170 that is attached to the wall 1180. One advantage of attaching the plate 1110 to the mounting plate 1190 can be that the plate 1110 can be easily and/or quickly removed from the mounting plate 1170 for maintenance, upgrades, replacement, and so forth. In one embodiment, the plate 1110 can be attached to the mounting plate 1170 using one or more fasteners or connectors, such as hooks, quick connectors, screws, bolts, and so forth.

In one embodiment, the wireless transfer station can monitor an amount of energy and/or data transmitted by a wireless transfer coil and/or an amount of energy and/or data received by the wireless transfer coil. In one example, a first wireless transfer station with a receiving coil can communicate energy information to a second wireless transfer station with a transmitting coil, using a communications module as discussed in the preceding paragraphs. The energy information can include: voltage level information, current draw level information, energy level information of the energy received at the receiving coil, energy level information of the energy transmitted from the transmitting coil, internal temperature information, ambient temperature information, or other types of desired metrics.

In one embodiment, the wireless transfer station can adjust an amount of energy transmitted from a wireless transfer coil of a wireless transfer station to another wireless transfer coil of another wireless transfer station based on the energy information. In one example, if a device with an integrated or coupled wireless transfer station requires 5 volts (V) and 2 amps (A) of energy and is currently receiving a voltage level or an amperage level at a level above or below a selected energy level range (such as a voltage range and/or a current range), the device or the coupled wireless transfer station can communicate the energy information to the wireless transfer station. In this example, the wireless transfer station can adjust the energy transferred from the wireless transfer coil to the other wireless transfer coil to bring the energy level range received at a wireless transfer coil to a level within a selected energy level range.

In another embodiment, a wireless transfer station can be a communication hub between multiple devices and/or other wireless transfer stations. In one example, the wireless transfer station can be integrated into a medical cart. The medical cart can receive data from a first device using a communication module (as discussed in the preceding paragraphs) and relay the data to another wireless transfer station, such as a wireless transfer station attached to a wall or floor.

In one embodiment, the wireless transfer station can regulate an amount of energy received by one or more other wireless transfer stations. In one example, when a first wireless transfer station uses a wireless transfer coil to transfer energy, the first wireless transfer station can control the amount of energy received at a second wireless transfer station by detuning a frequency of the wireless transfer coil of the first wireless transfer station by a selected amount. In another example, the first wireless transfer station can control the amount of energy received from the second wireless transfer station by detuning a frequency of the wireless transfer coil of the first wireless transfer station by selected amount.

Figure 12:
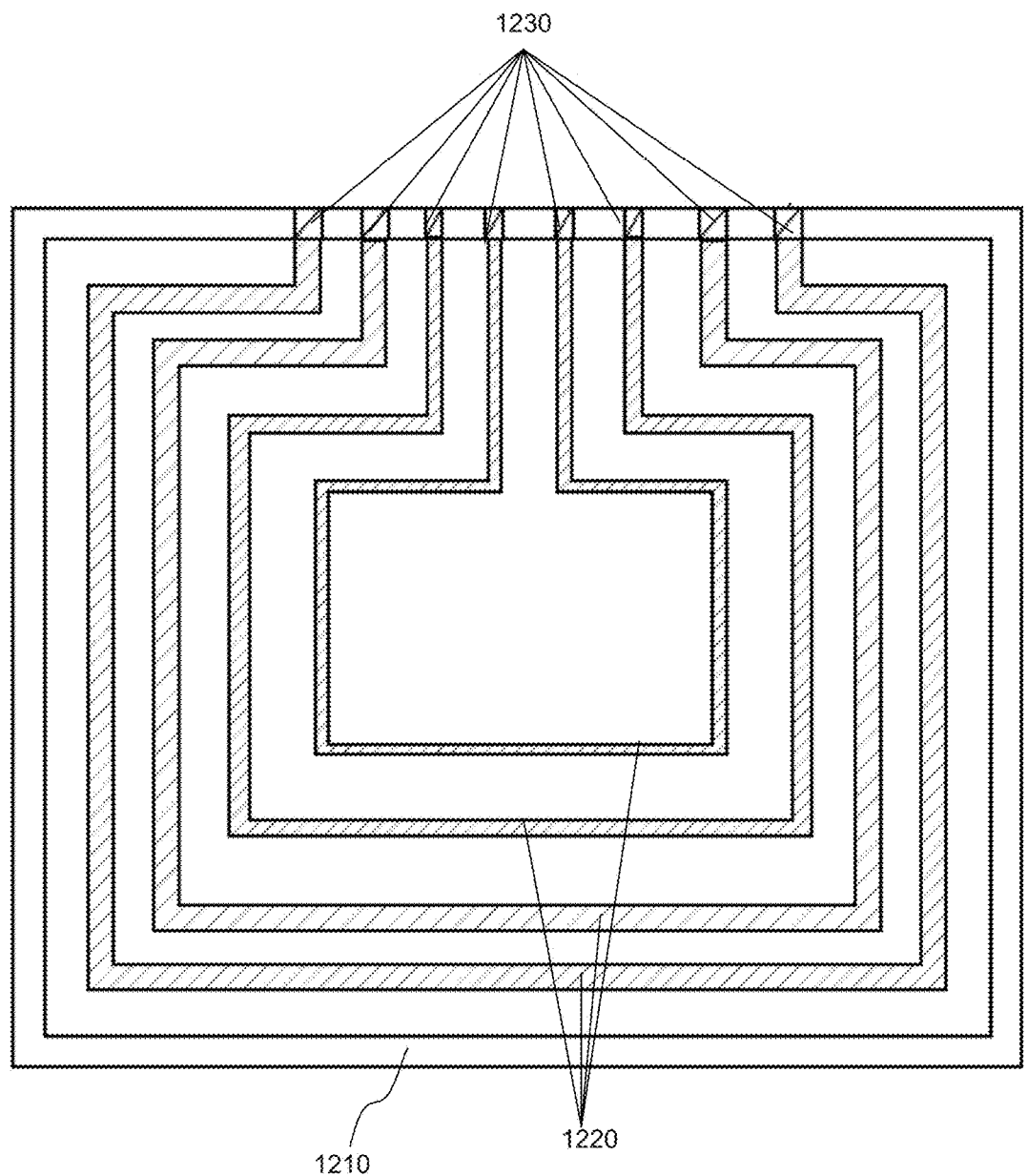
FIG. 12 depicts a wireless transfer coil with a plurality of loops or winds in accordance with an example.

FIG. 12 shows a wireless transfer coil 1210 with a plurality of loops or winds 1220. In one embodiment, an amount of energy transmitted and/or received by the wireless transfer coil 1210 can be adjusted using one or more adjustment modules 1230. In one embodiment, the one or more adjustment modules 1230 can engage or disengage one or more of the plurality of loops 1220 to: effectively vary a size of the wireless transfer coil 1210; change a number of active loops of the wireless transfer coil 1210; change a shape of a magnetic field of the wireless transfer coil 1210; change an amount of energy transferred using the wireless transfer coil 1210; or enable or disable selected devices from receiving energy and/or data from the wireless transfer coil 1210.

In one embodiment, the one or more adjustment modules 1230 can be one or more switches, such as an impedance matching switch or an on/off switch. In one example, a selected number of the plurality of loops 1220 can be engaged by turning on one or more of the corresponding switches and a selected number of the plurality of loops 1220 can be disengaged by turning off one or more of the corresponding switches.

In one embodiment, a resonant frequency between of the wireless transfer coil 1210 can be dynamically adjusted using the one or more adjustment modules 1230. In one embodiment, the one or more adjustment modules 1230 can be adjustable energy oscillators. In another embodiment, the one or more adjustment modules 1230 can be variable capacitors, variable inductors, and/or variable inductors and the respective capacitance, resistance, and/or inductance can be changed to tune or detune the wireless transfer coil 1210.

In one embodiment, a wireless transfer coil of a first wireless transfer station can have a fixed impedance and/or resonant frequency and an impedance and/or resonant frequency of a second wireless transfer coil of a second wireless transfer station can be adjustable. In another embodiment, the impedance and/or resonant frequency of the wireless transfer coil of the first wireless transfer station and the impedance and/or resonant frequency of the wireless transfer coil of the second wireless transfer station can each be adjustable.

Traditionally, wireless energy or data transfer using wireless transfer coils has been limited because of alignment requirements. Depending on a level of misalignment between wireless transfer coils, a receiving coil may only receive a partial amount of energy from a transmitting coil or receive substantially none of the energy transferred from the transmitting coil. Additionally, a wireless energy transfer has traditionally been limited by a distance between the transmitting coil and the receiving coil.

Figure 13:
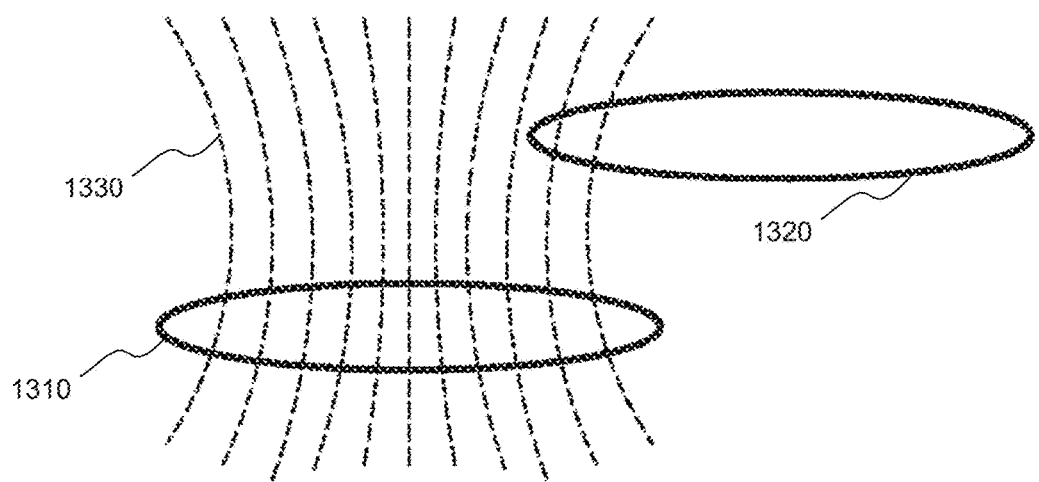
FIG. 13 depicts a first wireless transfer coil emitting a magnetic field and a second wireless transfer coil that is partially aligned or partially coupled with the magnetic field of the first wireless transfer coil in accordance with an example.

FIG. 13 shows a first wireless transfer coil 1310 emitting a magnetic field 1330 and a second wireless transfer coil 1320 that is partially aligned or partially coupled with the magnetic field 1330 of the first wireless transfer coil 1310. In one example, the first wireless transfer coil 1310 can be configured to emit the magnetic field 1330 with a selected field range. In this example, when the second wireless transfer coil 1320 is only partially located within the magnetic field 1330, the second wireless transfer coil 1320 may only be partially aligned or partially coupled. In one embodiment, when the second wireless transfer coil 1320 is only partially aligned or partially coupled, the second wireless transfer coil 1320 may receive a partial data and/or energy transfer or substantially no data and/or energy transfer.

In one embodiment, an efficiency of a transfer of energy between a first wireless transfer station and a second wireless transfer station using magnetic inductive coupling or magnetic resonant coupling is inversely proportional to a spatial separation between a transmitting coil of the first wireless transfer station and a receiving coil of the second wireless transfer station. As previously discussed, placing the wireless transfer stations within the near field distance limits can substantially increase the efficiency of the energy transfer.

Returning to FIG. 12, in one embodiment, the wireless transfer station can use a combination of techniques to adjust: a size, a shape, and/or a coverage range of a magnetic field of the wireless transfer coil 1210; a coupling distance between a transmitting coil and a receiving coil; and/or a range of alignment positions of the receiving coil relative to the transmitting coil. In one example, the wireless transfer station can include an array of multiple wireless transfer coils and/or Ferrite material, as discussed in the proceeding paragraphs. In one embodiment, the Ferrite material can be used to adjust a size, a shape, and/or a coverage range of a magnetic field of one or more wireless transfer coils 1210. In another embodiment, the wireless transfer station can change an amount of energy provided to one or more wireless transfer coils in a wireless transfer coil array by adjusting a size, a shape, and/or a coverage range of the magnetic field.

In one embodiment, to adjust a threshold coupling distance between a transmitting coil of a first wireless transfer station and a receiving coil of a second wireless transfer station, a size of the transmitting coil of the first wireless transfer station can be adjusted and/or a size of the receiving coil of the second wireless transfer station can be adjusted. In another embodiment, to adjust a range of alignment positions, angles, and/or locations of the receiving coil relative to the transmitting coil, the size or the shape of the transmitting coil and/or the receiving coil can be adjusted.

In one embodiment, one or more adjustment modules 1230 can adjust a size or a shape of a wireless transfer coil 1210, such as the transmitting coil and/or the receiving coil. In one example, a selected number of the plurality of loops 1220 can be engaged or disengaged by using the one or more adjustment modules 1230 to adjust the size and/or shape of the wireless transfer coil 1230. In one embodiment, a size of a magnetic field can correspond to a size of the wireless transfer coil 1230. In one example, as the size of the wireless transfer coil 1210 increases the size of the magnetic field also increases, and vice versa. In one embodiment, one or more adjustment modules 1230 can adjust a transmitting coil size to create a selected magnetic field size.

In one embodiment, a resonant frequency between one or more wireless transfer coils 1210 can be dynamically adjusted using the one or more adjustment modules 1230. In another embodiment, the size and/or shape of the magnetic field can be adjusted by changing an orientation of the transmitting coil. In another embodiment, the size and/or shape of the magnetic field can be adjusted using Ferrite material. In one embodiment, the one or more adjustment modules 1230 of a wireless transfer station can dynamically adjust a size and/or a shape of a magnetic field (such as an electromagnetic field) of one or more wireless transfer coils 1210 based on a location where the wireless transfer station is used or an environment where the wireless transfer station is used.

In one embodiment, the size and/or shape of the magnetic field of a wireless transfer station can be adjusted using a phased array of multiple wireless transfer coils. In one example, the phased array of the multiple wireless transfer coils can be a plurality of transmitting coils configured for resonant coupling arranged in a form of an array, e.g. a transmitter resonant phased array. In another embodiment, each of the wireless transfer coils 1210 in the phased array can be associated with one or more adjustment modules 1230, such as selected capacitors. A selected wireless transfer coil 1210 and an associated one or more adjustment modules 1230 can form a tuned circuit that can be tuned to a selected frequency or frequency range. In another embodiment, each of the plurality of wireless transfer coil 1210 can be adjusted to transmit energy at different frequency levels and/or energy levels.

In one embodiment, a wireless transfer station can use a plurality of resonant frequencies to transfer energy to one or more devices or one or more other wireless transfer stations. In another embodiment, the wireless transfer station can provide different amounts of energy to different devices or other wireless transfer stations at different resonant frequencies. In one example, a first wireless transfer station can receive wireless energy from a primary wireless transfer station at a first resonant frequency and a second wireless transfer station can receive wireless energy from the primary wireless transfer station at a second resonant frequency.

In one embodiment, the primary wireless transfer station can set priority levels for the different devices or other wireless transfer stations receiving wireless energy at different resonant frequencies. In one example, a first wireless transfer station with a highest priority can receive wireless energy from the primary wireless transfer station at a first selected resonant frequency and a second wireless transfer station with a lower priority can receive wireless energy from the primary wireless transfer station at a second selected resonant frequency.

In one embodiment, the primary wireless transfer station may not have the capability to provide wireless energy to all the devices and/or other wireless transfer stations requesting wireless energy transfer. When the primary wireless transfer station does not have the capability to support all of the and/or other wireless transfer stations requesting wireless transfer requesting wireless energy transfer, the primary wireless transfer station can transfer energy to selected devices based on an energy transfer priority. In one embodiment, the primary wireless transfer station can select different resonant frequencies to transfer energy to different devices based on the energy transfer priority of the device. In one example, the primary wireless transfer station can be capable of supporting energy transfer for a combination of up to 5 devices and/or other wireless transfer stations and 10 devices and other wireless transfer stations can request wireless energy transfer. In this example, the primary wireless transfer station can determine the priority of the 10 devices and/or other wireless transfer stations and select 5 devices and/or other wireless transfer stations to transfer energy to. The primary wireless transfer station can select one or more resonant frequencies to transfer energy to the 5 devices. The remaining devices can be de-selected (e.g. not selected) for charging by not tuning transmitting coils to frequencies of the remaining devices. In one embodiment, the remaining devices can be selected and charged after the first 5 have been charged.

In one embodiment, a transmission frequency of a wireless transfer coil of a wireless transfer station for transferring wireless energy can be based on a natural frequency of the wireless transfer station, a device, and/or a wireless transfer coil wireless of another wireless transfer station.

In one embodiment, each wireless transfer station can have a unique station ID associated with the wireless transfer station. In another embodiment, each station ID can be used to associate selected information with each wireless transfer station. In another embodiment, each wireless transfer station and/or each type of wireless transfer station can be configured to have a plurality of different characteristics, such as different form factors, different voltage inputs and/or outputs, different current inputs and/or outputs, and so forth.

In one embodiment, each rechargeable battery or battery cell in a wireless transfer station can have a different battery ID. In another embodiment, one or more types of rechargeable batteries or battery cells in a wireless transfer station can each have different battery IDs. In another embodiment, a wireless transfer station can be coupled to a plurality of different types of devices and/or other wireless transfer stations. In one example, the different types of devices and/or other wireless transfer stations can include: devices and/or other wireless transfer stations used for selected applications, devices and/or other wireless transfer stations with different voltage inputs or outputs, devices and/or other wireless transfer stations with different current inputs or outputs, and so forth. In another embodiment, the different types of devices can use different types of wireless transfer stations. In another embodiment, different station IDs for different wireless transfer stations can be associated with selected types of devices. In one example, each device and/or wireless transfer station can determine when a wireless transfer station coupled to the device is a wireless transfer station that is compatible with the device using the station ID of the wireless transfer station and/or the device ID of the device. In one embodiment, a device ID, a station ID, and/or a battery ID can include: serial number information of the device, the station, or the battery; a manufacturing date of the device, the station, or the battery; a manufacturing location of the device, the station, or the battery; and/or a version number of the device, battery, or wireless transfer station, respectively.

In one embodiment, wireless energy transferred between a first wireless transfer station and a second wireless transfer station can be an AC energy. In another embodiment, the first wireless transfer station can send the AC energy to the second wireless transfer station, and the second wireless transfer station can convert the AC energy into a direct current (DC) energy. In one example, the second wireless transfer station can be a wireless energy battery pack. In this example, the wireless energy battery pack can include a built-in charger to convert the received AC energy to a DC energy and transfer the DC energy to one or more batteries or battery cells of the wireless energy battery pack.

In one embodiment, a wireless transfer station can include a wave rectifier to adjust (e.g. step up or step down) a voltage level and/or current level of the transferred energy. In one embodiment, the wireless transfer station can include a buck converter, wherein the wave rectifier can transfer the wireless energy to one or more batteries or one or more battery cells via the buck converter. In another embodiment, a current level or voltage level of the wireless transfer station can be controlled using a stepper, such as a current stepper and/or a voltage stepper respectively. In another embodiment, the wireless transfer station can use a sensor resistor to measure a current going into one or more batteries or to a device.

In one embodiment, a first wireless transfer station can communicate voltage level information and/or current level information with a second wireless transfer station using a communication module. In one example, the first wireless transfer station can receive the voltage level and/or current level information from the second wireless transfer station and adjust the voltage level and/or current level of the wirelessly transferred energy to the second wireless transfer station based on the voltage level and/or current level information. In another embodiment, the first wireless transfer station and/or the second wireless transfer station can use a shunt or voltage stepper to control an amount of energy transferred between the first wireless transfer station and the second wireless transfer station.

Figure 14A:
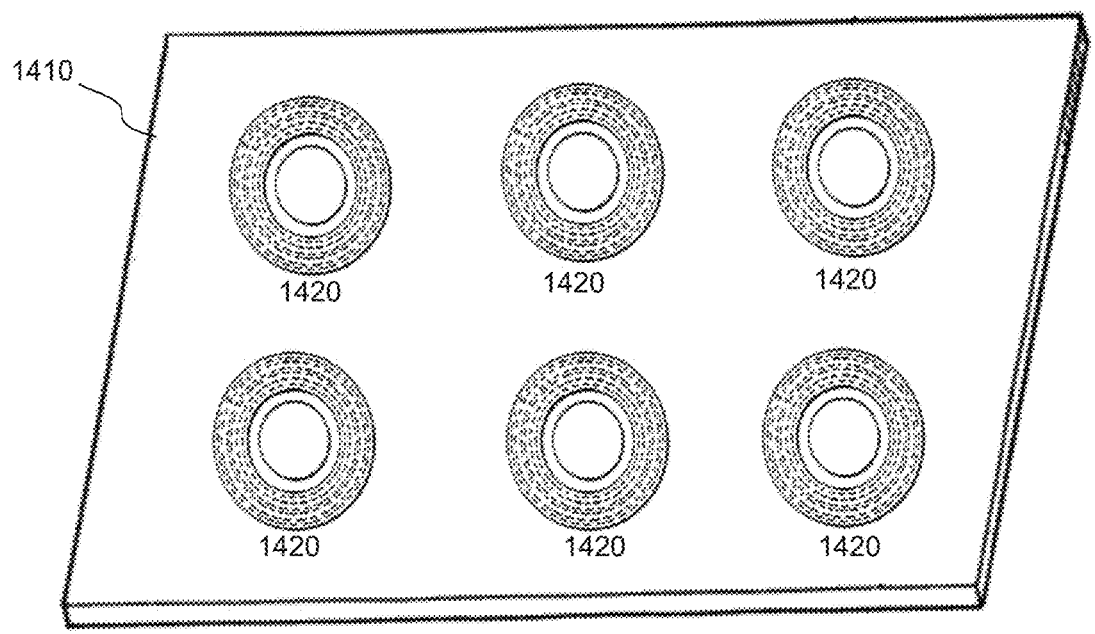
FIG. 14a depicts a wireless transfer station with a plurality of wireless transfer coils in accordance with an example.

FIG. 14a shows a wireless transfer station 1410 with a plurality of wireless transfer coils 1420. In one embodiment, the plurality of wireless transfer coils 1420 can be used to transfer energy and/or data to a device and/or another wireless transfer station.

In one example, the wireless transfer station 1410 can use a plurality of wireless transfer coils 1420, such as transmitting coils, to transfer energy to one or more wireless transfer coils of one or more other wireless transfer stations and/or devices using the plurality of wireless transfer coils 1420. In one example, the wireless transfer station 1410 can have 5 wireless transfer coils 1420 and can transfer energy simultaneously to receiving coils of 5 different wireless transfer stations and/or devices. In another example, the wireless transfer station 1410 can have 5 wireless transfer coils 1420 and can transfer energy to one wireless transfer station using a selected number of wireless transfer coils, such as 3 of the wireless transfer coils 1420 and transfer energy to a device using a second number of wireless transfer coils, such as 2 of the wireless transfer coils 1420. In another embodiment, the wireless transfer coils 1420 can include one or more wireless repeater coils to relay energy from a first energy source, such as a first wireless transfer station, to a device. One advantage of transferring energy from a wireless transfer station 1410 using the plurality of wireless transfer coils 1420 is to increase the overall current and/or voltage received by receiving coils of another wireless transfer station or device.

Figure 14B:
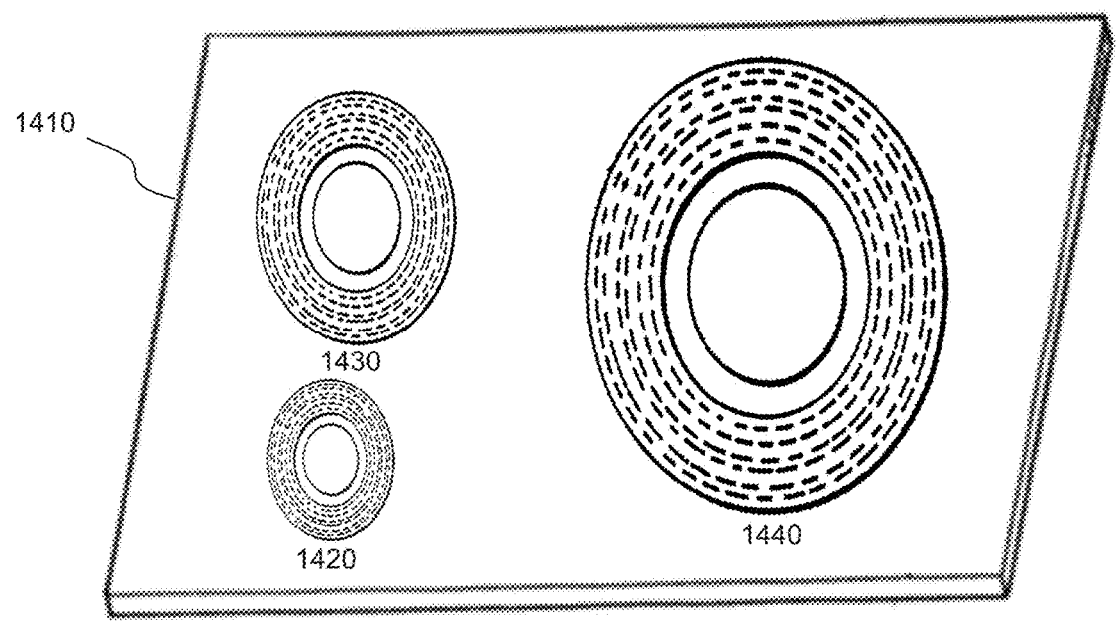
FIG. 14b depicts a wireless transfer station with a plurality of wireless transfer coils that are different sizes in accordance with an example.

FIG. 14b shows a wireless transfer station 1410 with a plurality of wireless transfer coils 1420, 1430, and 1440 that are different sizes. In one embodiment, the plurality of wireless transfer coils 1420, 1430, and 1440 that are different sizes can be used to transfer energy and/or data to devices and/or other wireless transfer stations with corresponding wireless transfer coil sizes. In one example, the wireless transfer station 1410 can use wireless transfer coil 1420 to transfer energy to a selected device and use wireless transfer coil 1430 to transfer data with a selected wireless transfer station.

Figure 15A:
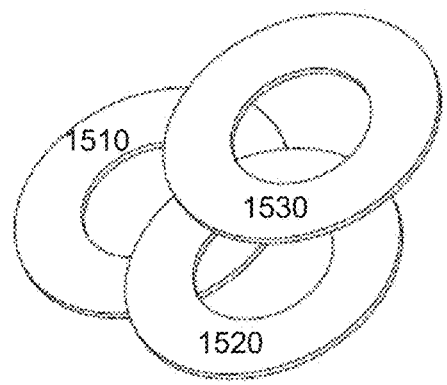
FIG. 15a depicts a wireless transfer coil with overlapping wireless transfer coils in accordance with an example.
Figure 15B:
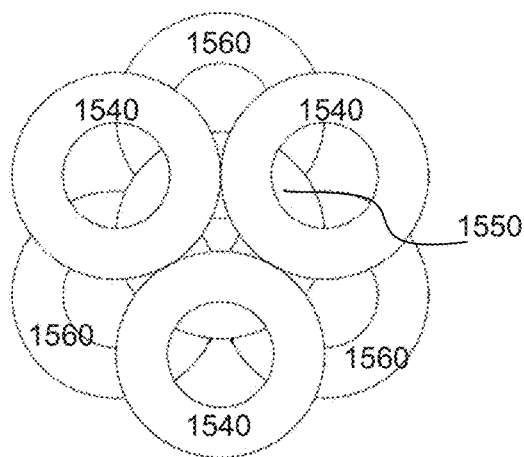
FIG. 15b depicts layers of wireless transfer coils in accordance with an example.
Figure 15C:
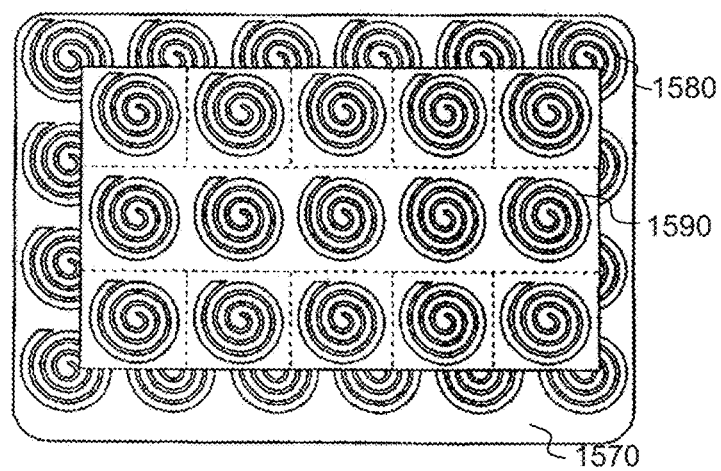
FIG. 15c depicts a wireless transfer station with overlapping wireless transfer coil arrays in accordance with an example.

FIGS. 15a, 15b, and 15c provide examples of wireless transfer coils in overlapping patterns. FIG. 15a shows a wireless transfer coil 1530 with overlapping wireless transfer coils 1510 and 1520. FIG. 15a further shows wireless transfer coil 1520 overlapping wireless transfer coil 1510. FIG. 15b shows layers of wireless transfer coils 1540, 1550, and 1560. FIG. 15b further shows one exemplary embodiment of layers of wireless transfer coils with a bottom layer of wireless transfer coils 1560, a middle layer of wireless transfer coils 1550, and a top layer of wireless transfer coils 1540. FIG. 15c shows a wireless transfer station 1570 with overlapping wireless transfer coil arrays 1580 and 1590, as further discussed in the proceeding paragraphs. One advantage of overlapping the wireless transfer coils can be to shape an overall magnetic field from a plurality of wireless transfer coils.

Figure 16:
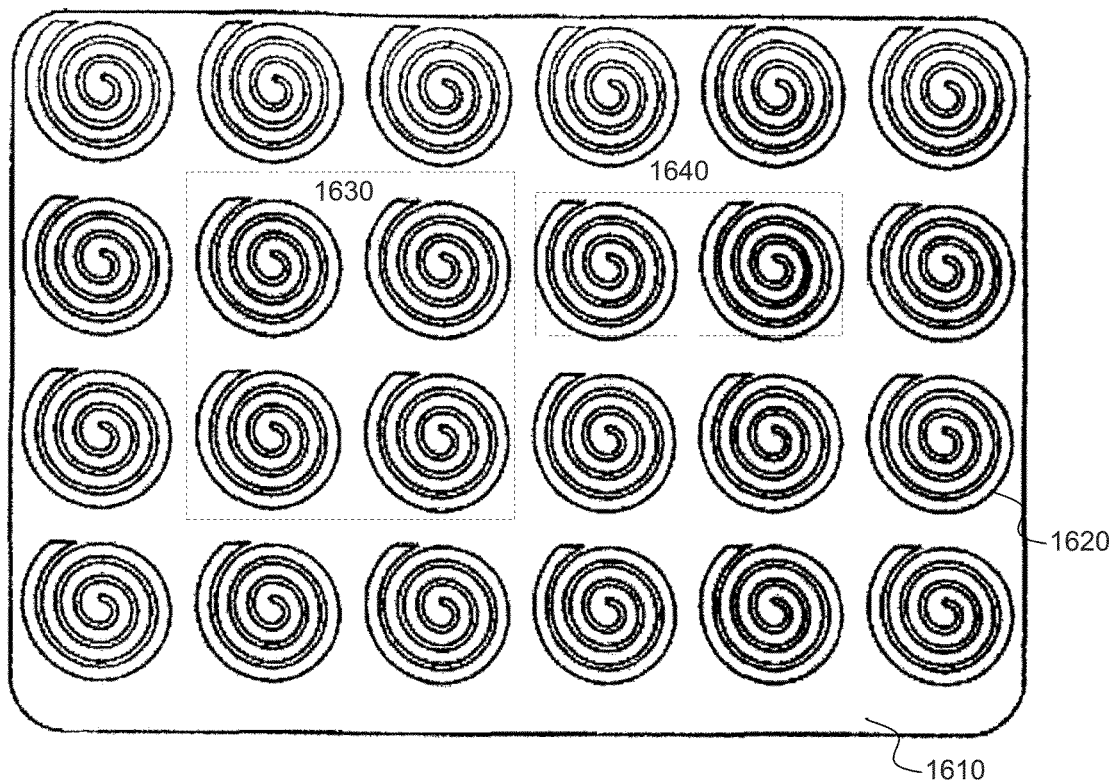
FIG. 16 depicts a wireless transfer station with an array of wireless transfer coils in accordance with an example.

In one embodiment, to increase a coupling distance range between a transmitting coil and a receiving coil and/or to increase a range of alignment positions between a transmitting coil and a receiving coil, a transmitting coil array and/or a receiving coil array can be used. FIG. 16 show a wireless transfer station 1610 with an array of wireless transfer coils 1620. In one embodiment, the wireless transfer coils of the array 1620 can be arranged in a selected pattern, i.e. a coil array pattern. In one example, the wireless transfer coils of the array 1620 can be arranged in a rectangular pattern (such as in FIG. 16), a circular pattern, an elliptical pattern, and so forth. FIG. 16 shows a wireless transfer station 1610 with a non-overlapping wireless transfer coil array pattern. In one embodiment, the wireless transfer coil array can include an array of transmitting coils, receiving coils, repeater coils, or a combination thereof. One advantage of non-overlapping wireless energy coils can be to create separate electromagnetic fields.

In one embodiment, the wireless transfer station can select a number of wireless transfer coils in the coil array, e.g. a wireless transfer coil array subset, to provide energy for wireless energy transfer. FIG. 16 further shows the wireless transfer station 1610 with wireless transfer coil subsets 1630 and 1640 within the wireless coil array 1620. In one embodiment, the wireless transfer station 1610 can select a number of wireless transfer coils, e.g. a wireless transfer coil subset. In one example, the wireless transfer station 1610 can receive or transmit energy using one or more wireless transfer coil subsets 1630 and 1640 within the wireless coil array 1620 and not receive or transmit energy using the other wireless transfer coils in the wireless coil array 1620. FIG. 16 shows a wireless transfer coil subset 1630 with four selected wireless transfer coils in the wireless transfer coil subset 1630 and wireless transfer coil subset 1640 with two selected wireless transfer coils in the wireless transfer coil subset 1640. Subsets 1630 and 1640 are exemplary embodiments of different numbers of selected wireless transfer coils in a wireless transfer coil subsets. The number of selected wireless transfer coils in a wireless transfer coil subset is not limited to the number of coils in subsets 1630 and 1640 of FIG. 16.

In another embodiment, the wireless transfer station 1610 can detect a location of one or more receiving coils relative to one or more transmitting coils in the wireless coil array 1620. When the location of the one or more receiving coils is determined relative to the one or more transmitting coils, the wireless coil array 1620 can provide energy to the one or more wireless transfer coils or a wireless transfer coil array subset, such as wireless transfer coil subset 1630 or 1640, corresponding to the location of the one or more receiving coils. One advantage of providing power to the one or more wireless transfer coils or the wireless transfer coil array subset corresponding to the location of the one or more receiving coils can be to increase or optimize an amount of energy received at the one or more receiving clients.

In one embodiment, to detect the location of the one or more receiving coils of a device or another wireless transfer station relative to one or more transmitting coils of the wireless transfer station 1610, the wireless transfer station 1610 can be in communication with the device or the other wireless transfer station. In one example, the other wireless transfer station can send a beacon to the wireless transfer station 1610 indicating a location of the other wireless transfer station or one or more receiving coil of the other wireless transfer station relative to the one or more wireless transfer coils or the wireless transfer coil array subset. In another embodiment, the wireless transfer station 1610 can determine alignment information based on the beacon and indicate to a user alignment directions.

In one embodiment, to determine a number of transmitting coils in the array subset 1630 or 1640 to provide energy to, the wireless transfer station 1610 can serially or sequentially applying energy to one or more wireless transfer coils in the wireless coil array 1620. Another wireless transfer station with one or more receiving coils can communicate energy information to the wireless transfer station 1610 when different transmitting coils are active and transferring energy. The wireless transfer station 1610 can use the energy information to determine an optimal number and/or subset of the transmitting coils to provide energy to for optimal or increased energy transfer to the receiving coil of the other wireless transfer station.

In another embodiment, the wireless coil array 1620 can be an array of receiving coils. The wireless coil array 1620 can sequentially or serially connect a selected subset of receiving coils to a receiving energy source and determine an arrangement of a selected subset of receiving coils, such as subsets 1630 or 1640, to receive an increased or optimal amount of energy from one or more transmitting coils. In one embodiment, an energy management system can determine an optimal number of selected transmitting coils or selected receiving coils to activate for coupling or pairing to provide a device or a wireless transfer station with a selected level of energy.

In one embodiment, a wireless transfer station can use a location of a transmitting coil and/or the location of a receiving coil to determine alignment information, such as the alignment of a receiving coil relative to a transmitting coil. In one example, the wireless transfer station can use the alignment information to determine a direction to move a transmitting coil and/or a receiving coil to increase or optimize the energy received at the receiving coil from the transmitting coil. In one example, when a receiving coil of a device is located left of center of a transmitting coil of a wireless transfer station, the wireless transfer station or the device can determine that to increase the energy transfer to the receiving coil, the receiving coil can be moved to the right and/or the transmitting coil can be moved to the left.

In one embodiment, the wireless transfer station can indicate to a user of a device and/or another wireless transfer station with a wireless transfer coil the direction to move the wireless transfer coil to increase an alignment and/or energy transfer between a wireless transfer coil of the wireless transfer station and the wireless transfer coil of the device or the other wireless transfer station. In one embodiment, the wireless transfer station can determine the direction to move a wireless transfer coil by monitoring an energy level received at the wireless transfer coil of the wireless transfer station. In one example, if a receiving coil of a wireless transfer station is moved to the left and an energy received from a transmitting coil of another wireless transfer station decreases, the wireless transfer station can determine that the receiving coil can be moved to the right relative to the transmitting coil of the other wireless transfer station to increase the received energy.

In one embodiment, the wireless transfer station can determine a direction for a wireless transfer coil to move by monitoring an energy load on one or more wireless transfer coils, such as transmitting coils, of the wireless transfer station. In one example, when a transmitting coil is moved to the left and an energy load on the transmitting coil decreases, the wireless transfer station can determine that the transmitting coil can be moved to the right to increase the energy received at a receiving coil of another wireless transfer station. In another embodiment, a device and/or the other wireless transfer station can communicate energy information to the wireless transfer station. The wireless transfer station can use the energy information to determine the location of a wireless transfer coil of the wireless transfer station relative to a wireless transfer coil of the other wireless transfer station and provide alignment information to the user.

In one embodiment, a wireless transfer station can include a display or other sensory indicator for providing alignment directions to a user via a graphical user interface. In another example, the wireless transfer station can communicate the alignment directions to another device with a display or other sensory indicator for providing the alignment directions to the user.

Traditionally, wireless energy is transferred on a one-to-one basis between a transmitting coil and a receiving coil because of a low efficiency of wireless charging and an interruption in energy transfer, such as a voltage interruption or a current interruption, to a device as a number of devices within the magnetic field changes. In one embodiment, a wireless transfer station can adjust a voltage output level and/or a current output level of a transmitting coil based on a number of devices and/or other wireless transfer stations located within the magnetic field.

In one example, the wireless transfer station can detect when a voltage output level and/or a current output level of a transmitting coil has changed and adjust the voltage output level and/or the current output level of the transmitting coil to maintain a selected voltage output level and/or current output level. In one embodiment, the wireless transfer station can receive voltage information and/or current information from a device and/or another wireless transfer station and use the received voltage information and/or current information to determine an amount to change the voltage output level and/or the current output level of the magnetic field.

In one embodiment, a receiving coil can receive wireless energy from a plurality of transmitting coils. In one example, a receiving coil can be located between two transmitting coils. In this example, the receiving coil can receive 50 percent of the wireless energy required by a wireless transfer station from one of the transmitting coils and 50 percent of the wireless energy required by the wireless transfer station from the other transmitting coil. In another example, the receiving coil can receive a higher or lower amount of energy from one of the transmitting coils, such as 25 percent of the wireless energy required by the wireless transfer station from one of the transmitting coils and 75 percent of the wireless energy required by the wireless transfer station from the other transmitting coil. In one embodiment, the receiving coil can receive different amounts of energy from different transmitting coils based on: an alignment of the receiving coil relative to one or more transmitting coils, a location of the receiving coil relative to the one or more transmitting coils, a size of the receiving coil relative to a size of one or more of the transmitting coils, a number of receiving coils and/or transmitting coils in a coil array, and so forth.

Figure 17:
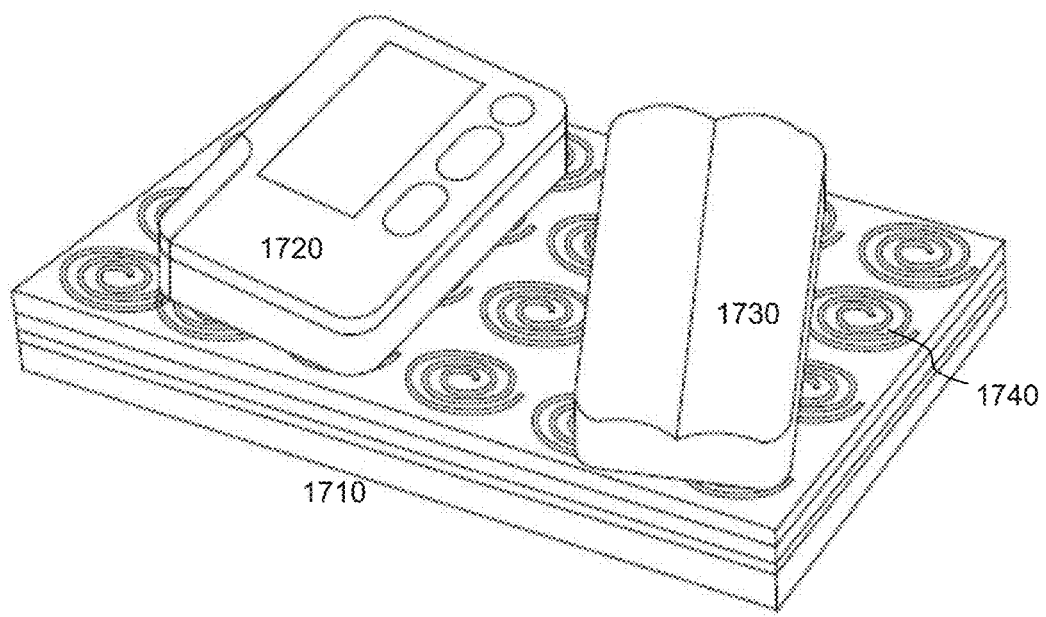
FIG. 17 depicts a wireless transfer hub transferring energy and/or information with an electronic device and/or another wireless transfer station using wireless transfer coils in accordance with an example.

In one embodiment, a wireless transfer station can be a wireless transfer hub (e.g. energy and/or data transfer) for a plurality of selected devices and/or other wireless transfer stations. FIG. 17 illustrates a wireless transfer hub 1710 transferring energy and/or information with an electronic device 1720, such as medical device, and/or another wireless transfer station 1730 using wireless transfer coils 1740. In one embodiment, the electronic device 1720 and the other wireless transfer station 1730 can exchange energy and/or information with the wireless transfer station 1710 at the same time or at different times. In another embodiment, the electronic device 1720 and the other wireless transfer station 1730 can transfer energy and/or information with the wireless transfer hub 1710 using different wireless transfer coils 1740.

In one example, the wireless transfer hub 1710 coupled to a medical cart can provide selected levels of energy to systems and subsystems of the medical cart and/or other devices coupled to the medical cart. In one embodiment, the wireless transfer hub 1710 coupled to the medical cart can receive energy and/or data from a wireless transfer station and relay the energy and/or data to systems and subsystems of the medical cart and/or other devices using one or more repeater coils.

In one embodiment, a medical cart or a device can have an integrated wireless transfer station to provide energy to systems and/or subsystems of the medical cart or the device when one or more external wireless transfer stations (e.g. non-integrated wireless transfer stations) are being recharged. In one embodiment, the integrated wireless transfer station can include a wireless transfer coils to receive energy and/or data from another wireless transfer station. In one example, the medical cart or the device can receive energy from the one or more external wireless transfer stations until an energy level of the one or more external wireless transfer stations is depleted or decreases below a threshold energy level. In this example, when the energy level of the one or more external wireless transfer stations is depleted or decreases below a threshold energy level, the medical cart or the device can be positioned adjacent a transmitter coil of another wireless transfer station and the one or more external wireless transfer stations can receive energy for recharging. In one embodiment, while the one or more external wireless transfer stations receive energy for recharging, the integrated wireless transfer station can provide energy to the medical cart or the device.

In one embodiment, the integrated wireless transfer station can receive energy from the other wireless transfer station to recharge one or more batteries of the integrated wireless transfer station. In another embodiment, the integrated wireless transfer station can receive energy from the one or more external wireless transfer stations to recharge the one or more batteries of the integrated wireless transfer station. In another embodiment, when the one or more external wireless transfer stations receive energy from another wireless transfer station, the one or more external wireless transfer stations can provide partial or full energy to the medical cart or the device.

In one embodiment, when the energy level of the one or more external wireless transfer stations is depleted or decreases below a threshold energy level, the one or more external wireless transfer stations can be removed from the medical cart or the device and placed adjacent a transmitter coil of another wireless transfer station to receive energy to recharge the external wireless transfer station. In one embodiment, while the one or more external wireless transfer stations are removed for recharging and/or until one or more other external wireless transfer stations are attached to the medical cart or the device, the integrated wireless transfer station can provide energy to one or more system or subsystem of the medical cart or the device. In one embodiment, when the medical cart or the device is placed adjacent to a transmitter coil of a wireless transfer station, the integrated wireless transfer station can receive energy from the wireless transfer station to recharge the integrated wireless transfer station.

In one embodiment, the medical cart or a device can include a wireless transfer coil to transfer energy and/or data with another wireless transfer station. In one example, the medical cart or a device can use the wireless transfer coil to receive energy and provide energy directly to one or more systems and/or subsystems of the medical cart or the device and/or provide energy to an energy source, such as a battery, of the medical cart or the device. In one example, the medical cart or the device with the wireless transfer coil can be placed near a transmitter coil of a wireless transfer station and the wireless transfer coil can relay energy to one or more systems and/or subsystems of the medical cart or the device.

Figure 18:
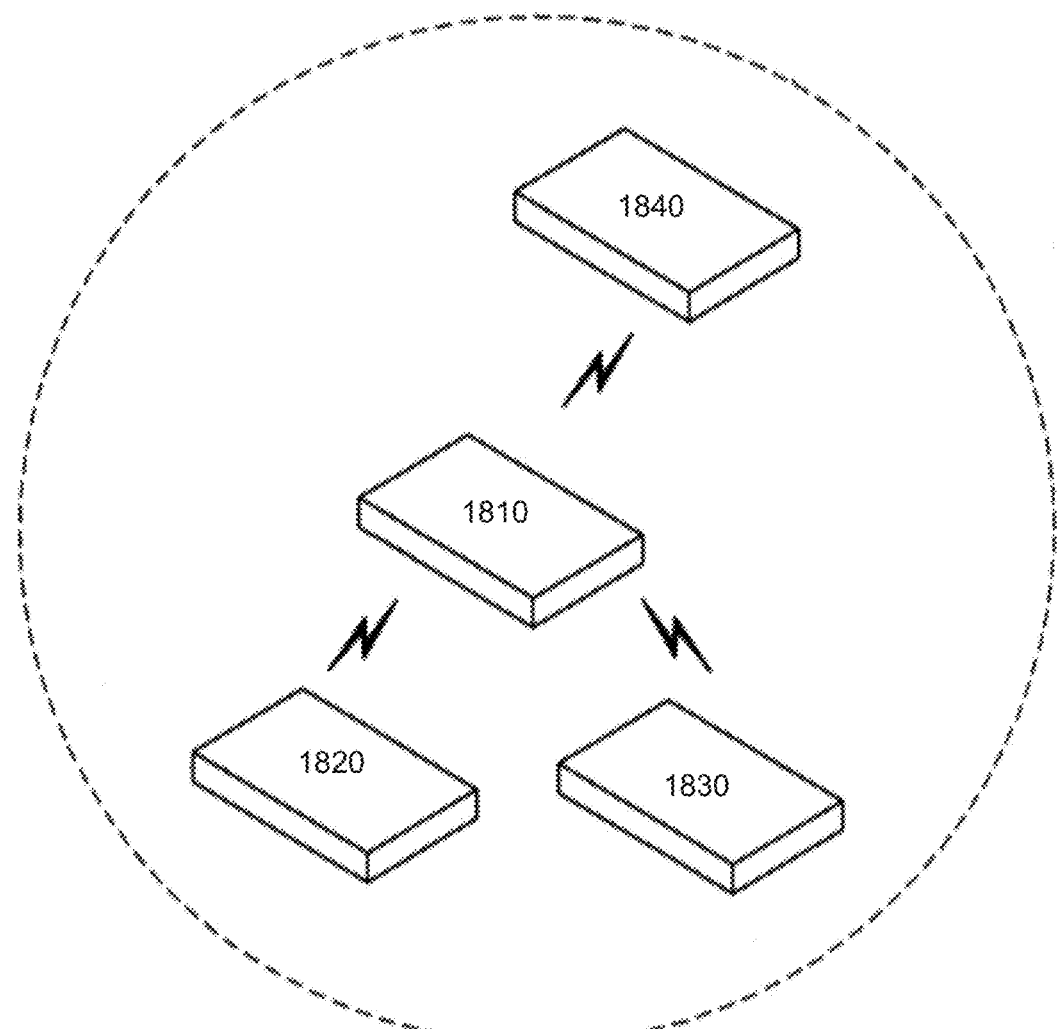
FIG. 18 depicts a wireless transfer station configured to communicate with other wireless transfer stations in accordance with an example.

FIG. 18 shows a wireless transfer station 1810 configured to communicate with other wireless transfer stations 1820, 1830, and/or 1840 and determine which of the one or more other wireless transfer stations 1820, 1830, and/or 1840 is capable and/or available to provide energy to a selected device and/or a selected wireless transfer station. In one example, the selected device or the selected wireless transfer station can send a wireless transfer request to the wireless transfer station. When the wireless transfer station 1810 is not compatible with the selected device or the wireless transfer station 1810 is not available to provide energy to the selected device, the wireless transfer station 1810 can communicate with the one or more other wireless transfer stations 1820, 1830, and/or 1840 to locate an available wireless transfer station of the one or more other wireless transfer stations 1820, 1830, and/or 1840 for the selected device or the selected wireless transfer station to receive wireless energy. When the wireless transfer station 1810 determines that available wireless transfer station can provide energy to the selected device or the selected wireless transfer station, the wireless transfer station 1810 can provide the selected device or the selected wireless transfer station with transfer station information for the available wireless transfer station.

In one embodiment, the transfer station information can include: directions to one of the other wireless transfer stations 1820, 1830, or 1840; authentication information to receive energy from the other wireless transfer stations 1820, 1830, or 1840; a number of available wireless transfer coils at the other wireless transfer stations 1820, 1830, or 1840; a type of wireless transfer coils available at the other wireless transfer stations 1820, 1830, or 1840; an energy capabilities of the other wireless transfer stations 1820, 1830, or 1840; and so forth. In one embodiment, when more than one of the other wireless transfer stations 1820, 1830, or 1840 are available to provide energy to the selected wireless transfer station or the selected device, the selected wireless transfer station or the selected device can select which one of the one or more other wireless transfer stations 1820, 1830, or 1840 to receive energy from based on charging criteria. The charging criteria can include: an energy output capability of each of the one or more available other wireless transfer stations 1820, 1830, or 1840; a location of each of the one or more available other wireless transfer stations 1820, 1830, or 1840; a distance from the selected device or the selected wireless transfer station to each of the one or more available other wireless transfer stations 1820, 1830, or 1840; a number of other devices or other wireless transfer stations receiving energy from each of the one or more available other wireless transfer stations 1820, 1830, or 1840, and so forth.

In one example, the wireless transfer station 1810 is not compatible with the selected device or the selected wireless transfer station when a wireless transfer coil of the selected device or wireless transfer coils of the selected wireless transfer station are a different shape or size than a wireless transfer coil of the wireless transfer station 1810. In another example, the wireless transfer station 1810 is not compatible with the selected device or the selected wireless transfer station when a wireless transfer coil of the selected device or a wireless transfer coil of the selected wireless transfer station receives data and/or wireless energy at a different resonant frequency range than a resonant frequency range of a wireless transfer coil of the wireless transfer station 1810.

Figure 19:
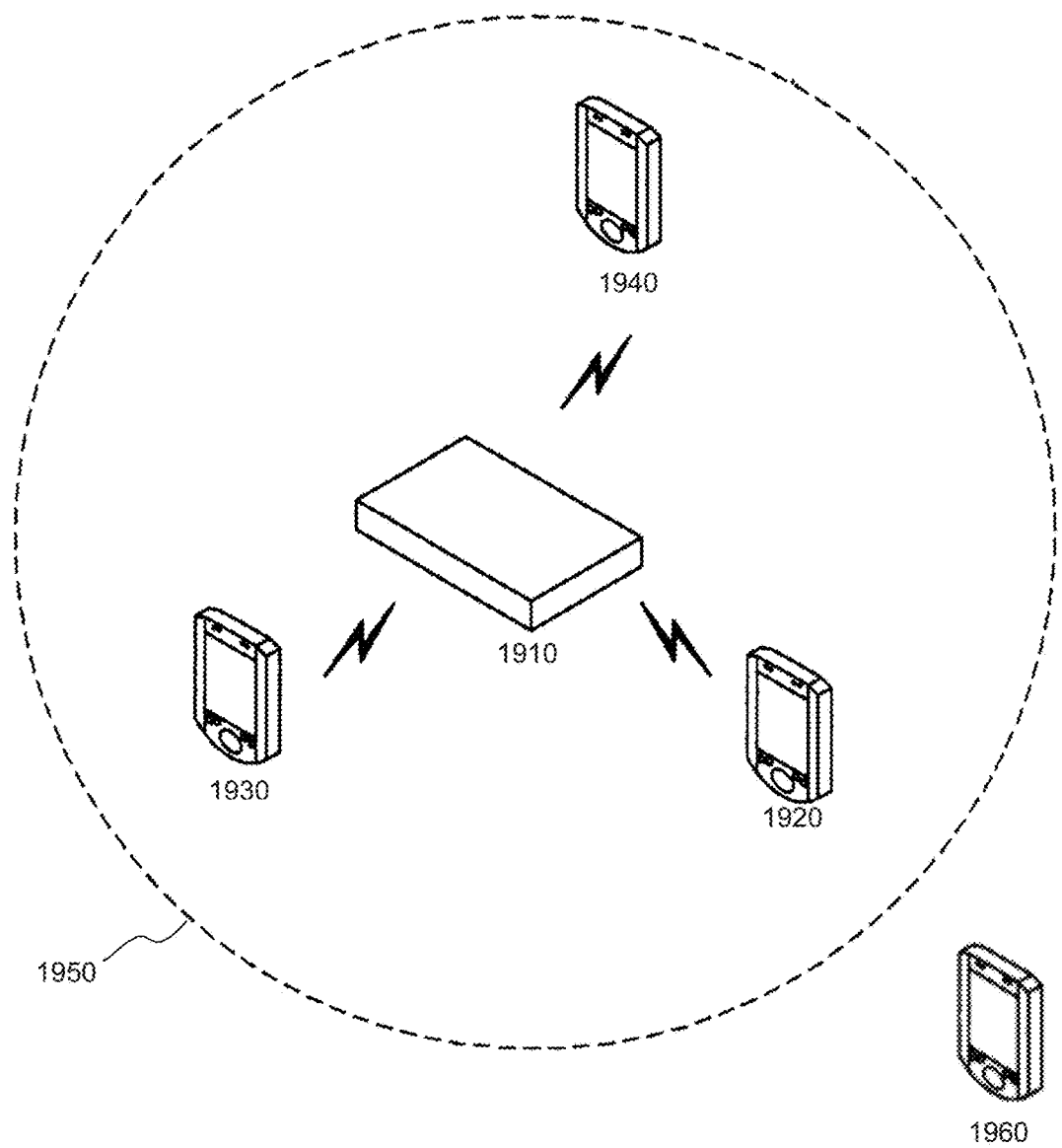
FIG. 19 depicts a wireless transfer station transferring energy and/or data with one or more wireless transfer stations and/or devices within a selected range in accordance with an example.

FIG. 19 shows a wireless transfer station 1910 transferring energy and/or data with one or more wireless transfer stations and/or devices 1920, 1930, and 1940 within a selected range 1950. In one embodiment, the wireless transfer station 1910 can adjust the selected range 1950 based on selected criteria, such as a number of wireless transfer stations and/or devices within a threshold range of the wireless transfer station 1910, a number of devices or other wireless transfer stations the wireless transfer station 1910 can support transferring energy and/or data to, and so forth. In one example, the wireless transfer station 1910 can transfer energy and/or data with wireless transfer stations and/or devices 1920, 1930, and 1940 that are within the selected range 1950 and not transfer energy and/or data with wireless transfer station and/or device 1960.

Traditionally, energy sources such as battery packs have different energy connectors for coupling the battery packs to different devices. Additionally, traditional battery packs have different energy connectors for different energy transfer levels. In one example, a battery coupled to a wheeled medical cart has one energy connector for transferring energy to the wheeled medical cart and a battery coupled to a medical fusion pump has a different energy connector for transferring energy to the medical fusion pump. Additionally, traditional battery packs for each type of device have different energy transfer levels corresponding to the device receiving the energy and require different battery pack configurations for each type of device. In one example, a wheeled medical cart may use a battery configured to transfer 20 volts and 5 amps of energy while a medical fusion pump may use a battery configured to transfer 10 volts and 3 amps. In one embodiment, a wireless transfer station can select the amount of energy, such as a voltage level or a current level, to wirelessly transfer to a device or other wireless transfer station based on a power configuration, such as a voltage or a current input requirement, of the device or other wireless transfer station. In one embodiment, the wireless transfer station can adjust or change an amount of energy transferred from the wireless transfer station to the device or other wireless transfer station by selecting different sizes of coils and/or tuning or detuning of coils (as discussed in the preceding paragraphs). In one example, the wireless transfer station can select a wireless transfer coil size or frequency to transfer 5 volts of energy to a 5-volt device and select a different wireless transfer coil size or frequency to transfer 10 volts of energy to a 10-volt device.

In one embodiment, the wireless transfer station can communicate with a device or another wireless transfer station and receive an energy requirement information of the device or the other wireless transfer station. The wireless energy battery pack can use the energy requirement information to determine the amount of energy to transfer to the device or the other wireless transfer station. In another embodiment, the wireless transfer station can receive a device ID or a station ID from the device or the other wireless transfer station, respectively, receiving energy from the wireless transfer station. The device ID or station ID can be associated with an energy requirement of the device or the other wireless transfer station and the wireless transfer station can adjust an energy level transfer based on the associated energy requirement.

One advantage of the wireless transfer station selecting the amount of energy to wirelessly transfer to a device or other wireless transfer station is that the wireless transfer station can be used with a plurality of different devices and/or other wireless transfer stations with different energy requirements. Another advantage of wireless transfer station having an adjustable energy level transfer capability can be to enable the wireless transfer station to be used with different devices and/or other wireless transfer stations with different energy level requirements without needing different energy connection adapters. In one example, the wireless transfer station can be connected to the wheeled medical cart, determine that the wheeled medical cart requires 20 volts and 5 amps of energy, and transfer the required energy. The wireless transfer station can later be swapped to a medical fusion pump, the wireless transfer station can determine the medical fusion pump requires 10 volts and 3 amps, and transfer the required energy.

In one embodiment, when a wireless transfer station that is transmitting wireless energy using a magnetic field can adjust a shape or a form a magnetic field using beamforming and/or field shaping.

In one embodiment, a wireless transfer station can shut off or enter sleep mode after a selected period of time. In another embodiment, when the wireless transfer station enters the sleep mode, the wireless transfer station stops transferring energy to one or more devices. One advantage of the wireless transfer station shutting off or entering sleep mode after a selected period of time can be to prevent the wireless transfer station from continuing to transmit wireless energy after a device in the wireless transfer station coverage area is fully charged. Another advantage of the wireless transfer station shutting off or entering sleep mode after a selected period of time can be to minimize the interference caused by the wireless energy transfer to communications between other devices.

In one embodiment, when the wireless transfer station enters sleep mode, the wireless transfer station stops transferring energy to all devices and monitors one or more presence sensors to detect when a device or other wireless transfer station that is capable of receiving wireless energy enters the coverage area of the wireless transfer station. In another embodiment, when the wireless transfer station enters sleep mode, the wireless transfer station stops transferring energy to all devices until the wireless transfer station receives a wireless transfer request from a device or other wireless transfer station. In another embodiment, the wireless transfer station can send a check-up message to one or more of the devices and/or other wireless transfer stations at selected times to determine when the one or more of the devices and/or other wireless transfer stations require an energy transfer. In one embodiment, the wireless transfer station can send the check-up message at a periodic interval.

In another embodiment, the wireless transfer station can shut off or enter sleep mode when the energy transfer load on the wireless transfer station decreases below a selected threshold. One advantage of the wireless transfer station shutting off or entering sleep mode when the energy transfer load on the wireless transfer station decreases below a selected threshold is that the wireless transfer station does not leak energy when a receiving device or other wireless transfer station does not require an energy transfer. The wireless transfer station can leak energy when a foreign object that has not requested an energy transfer and/or is not authorized to receive energy absorbs energy being transmitted to a device and/or other wireless transfer station.

In one embodiment, a device or other wireless transfer station can send a location beacon to the wireless transfer station to indicate the location of the device or the other wireless transfer station, such as a location of the device or the other wireless transfer station relative to the wireless transfer station. In one embodiment, the wireless transfer station can direct or guide a wireless energy transfer to the location indicated by the location beacon. One advantage of directing the wireless energy transfer, such as by using a location beacon, can be to minimize or eliminate interference caused by the wireless transfer station to other devices or systems. In one example, when the wireless transfer station determines a location of another wireless transfer station requesting energy transfer, the wireless transfer station can narrow the scope and/or direction of a field, such as a magnetic field, to be directed to the location of the other wireless transfer station. When the scope and/or direction of the field used wireless energy transfer can be limited, the field emitted for wireless energy transfer from the wireless transfer station may not interfere with other devices or other wireless transfer stations not located at a selected location for the wireless energy transfer.

In one embodiment, the wireless transfer station can trickle charge devices and/or other wireless transfer station. In one example, a fully charged battery of another wireless transfer station under no-load can be trickle charged by receiving energy at a rate equal to the discharge rate of the other wireless transfer station, e.g. maintaining a full battery capacity level of the other wireless transfer station. In another example, the other wireless transfer station can receive energy under a continuous float voltage charging, e.g. the amount of energy the other wireless transfer station receives can change according to an energy usage of the other wireless transfer station.

In another example, a device or another wireless transfer station can receive energy from the wireless transfer station at a rate lower than the energy usage level of the device or the other wireless transfer station. Although the lower energy rate may not provide enough energy to charge the device or the other wireless transfer station during use, the lower rate of energy can extend the usage life of the device or the other wireless transfer station, e.g. the amount of time a user can use the device or the other wireless transfer station before the device or the other wireless transfer station loses energy.

Figure 20:
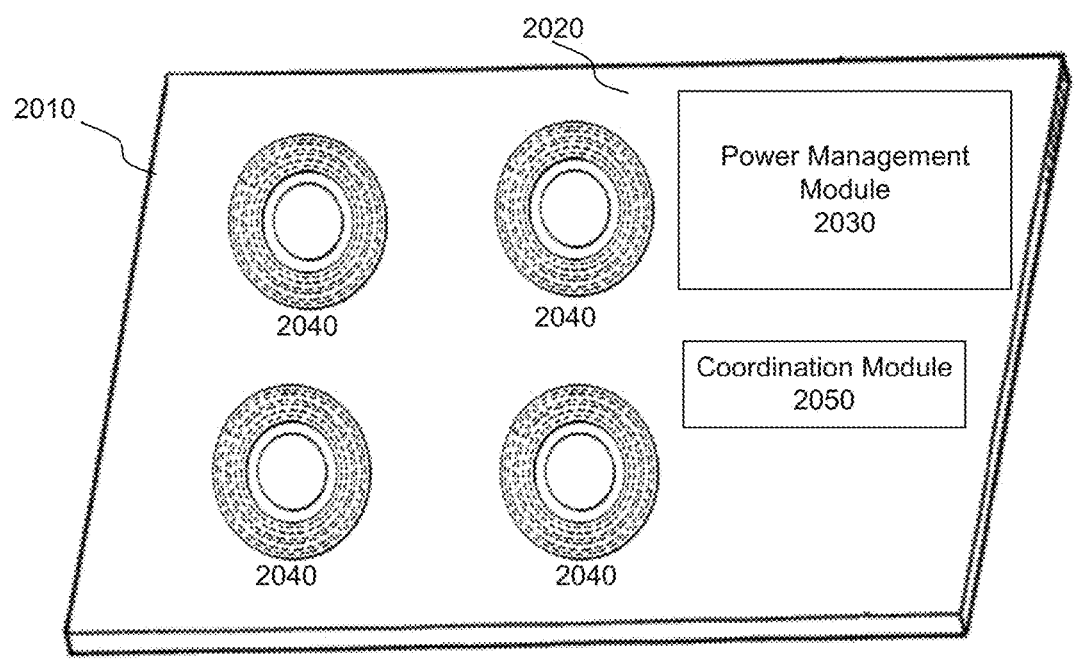
FIG. 20 depicts a wireless transfer station for wirelessly transferring energy in accordance with an example.

FIG. 20 shows a wireless transfer station 2010 for wirelessly transferring energy. In one embodiment, the wireless transfer station 2010 can include: an energy transfer platform 2020 having at least one surface for wirelessly transferring energy with a device or another wireless transfer station; a plurality of wireless transfer coils 2040 located within the energy transfer platform 2020, wherein the plurality of wireless transfer coils 2040 include at least one resonant charging coil and at least one inductive charging coil; and a power management module 2030 for controlling a plurality of wireless transfer coils.

In one embodiment, the plurality of wireless transfer coils 2040 can include a transmitting coil, a repeater coil, or a receiving coil. In another embodiment, the power management module 2030 is configured to select at least one of the plurality wireless transfer coils 2040 for transferring energy to the device or the other wireless transfer station. In another embodiment, the power management module 2030 is configured to adjust an amount of energy transferred from one or more of the plurality of wireless transfer coils 2040 to the device or the other wireless transfer station. In another embodiment, one of the plurality of wireless transfer coils 2040 is configured to transfer energy at a selected resonant frequency and another of the plurality of wireless transfer coils 2040 transfers energy at a different selected resonant frequency.

In one embodiment, the power management module 2030 is further configured to wirelessly transfer energy to the device or the other wireless transfer station using at least two wireless transfer coils of the plurality of wireless transfer coils 2040. In another embodiment, the power management module 2030 is further configured to wirelessly transfer a selected ratio of wireless energy from one of the at least two wireless transfer coils to the device or the other wireless transfer station. In another embodiment, the power management module 2030 is further configured to: wirelessly transfer energy to a first device or a first wireless transfer station using one of the plurality of wireless transfer coils 2040; wirelessly transfer energy to a second device or a second wireless transfer station using another of the plurality of wireless transfer coils 2040; and a coordination module 2050 configured to coordinate when energy is transferred to the first device or the first wireless transfer station and when energy is transferred to the second device or the second wireless transfer station. In another embodiment, the power management module 2030 is further configured to wirelessly transfer a first selected amount of energy to the first device or the first wireless transfer station and wirelessly transfer a second selected amount of energy to the second device or the second wireless transfer station.

Figure 21:
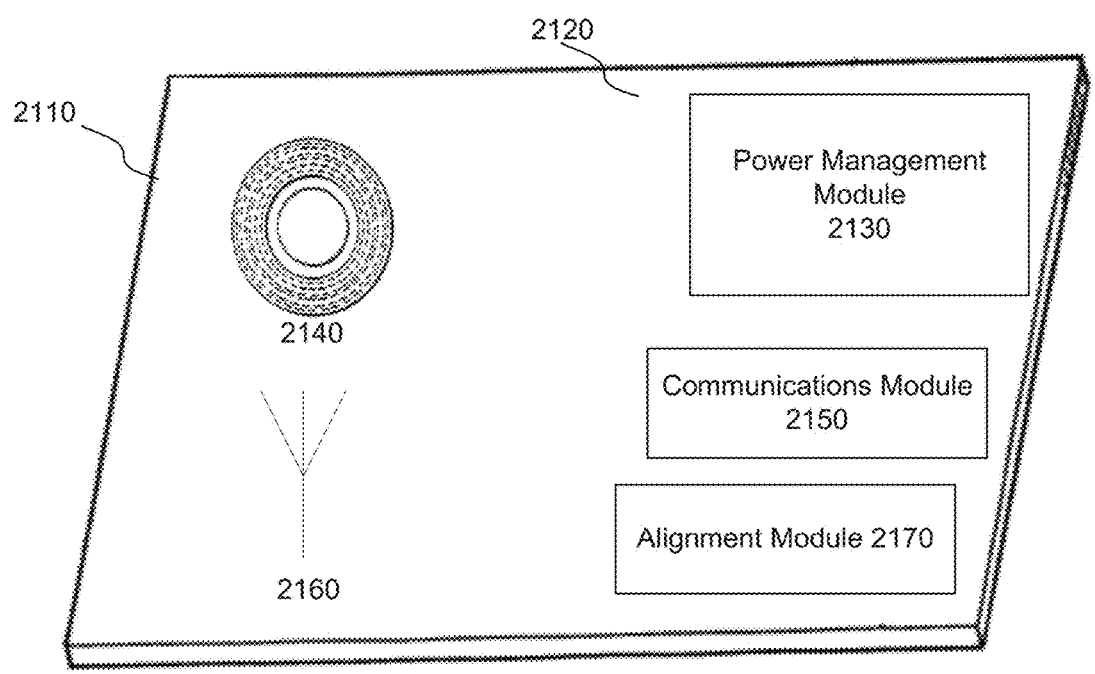
FIG. 21 depicts another wireless transfer station for wirelessly transferring energy in accordance with an example.

FIG. 21 shows a wireless transfer station 2110 for wirelessly transferring energy. In one embodiment, the wireless transfer station 2110 can include: at least one surface 2120 for wirelessly transferring energy with an electronic device or another wireless transfer station; a wireless transfer coil 2140 located adjacent to the at least one surface; an power management module 2130 for controlling the wireless transfer coil; and a communications module 2150 configured to communicate data between the wireless transfer station 2110 and the electronic device or the other wireless transfer station, wherein the communications module 2150 uses the wireless transfer coil 2140 or an antenna 2160 to communicate the data.

In one embodiment, the wireless transfer station 2110 is integrated into an electronic device, a wireless energy battery pack, a medical cart, a floor mat, a floor surface, a plate mounted to a wall, or a wall surface. In another embodiment, the wireless transfer station 2110 is configured to receive wireless energy from an additional wireless transfer station and communicate energy information to the additional wireless transfer station using the communications module 2150. In another embodiment, the wireless transfer station further includes an alignment module 2170 to determine an alignment of the wireless transfer coil 2140 relative to a wireless transfer coil of another wireless transfer station. In another embodiment, the power management module 2130 is configured to regulate an amount of energy the wireless transfer station 2110 receives from another wireless transfer station. In another embodiment, the wireless transfer station 2110 includes a plurality of wireless transfer coils 2140 and is configured to receive wireless energy using at least two of the plurality of wireless transfer coils 2140.

Figure 22:
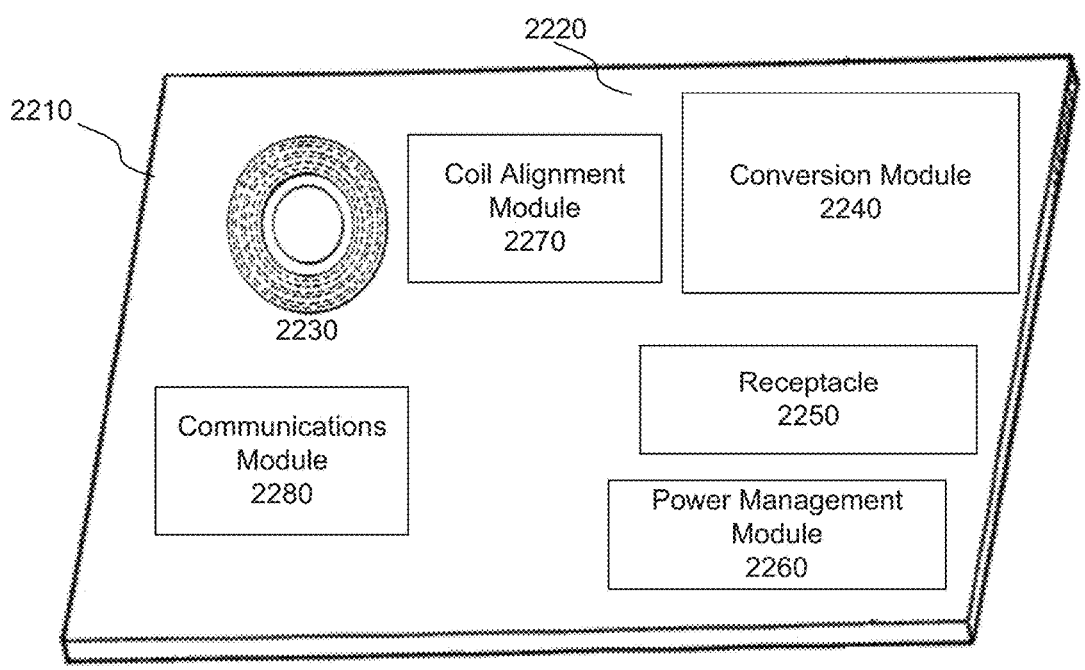
FIG. 22 depicts another wireless transfer station for wirelessly transferring energy in accordance with an example.

FIG. 22 shows a wireless transfer station 2210 for wirelessly transferring energy. In one embodiment, the wireless transfer station 2210 can include: an energy transfer platform 2220 having at least one surface; a wireless transfer coil 2230 located within the energy transfer platform for wirelessly transferring energy with another wireless transfer station; and a conversion module 2240. In one embodiment, the conversion module 2240 can be configured to switch the wireless transfer station 2220 between a transmit mode and a receive mode or switch the wireless transfer station 2220 between a resonance charging mode and an induction charging mode.

In one embodiment, the wireless transfer station 2210 can further comprise a receptacle 2250 to attach the other wireless transfer station to transmit or receive wireless energy with the wireless transfer station using the wireless transfer coil 2230. In another embodiment, the wireless transfer station 2210 can further comprise a power management module 2260 for controlling the wireless transfer coil 2230, wherein the power management module 2260 can dynamically adjust an amount of energy that the wireless transfer coil 2230 is configured to receive from an additional wireless transfer station. In another embodiment, the wireless transfer station can further comprise a coil alignment module 2270 configured to receive alignment information from the other wireless transfer station using a communications module 2280 and determine an alignment of the wireless transfer coil 2230 of the wireless transfer station 2210 relative to a wireless transfer coil of the other wireless transfer station using the alignment information. In another embodiment, the wireless transfer station 2210 of can further indicate alignment correction information to a user of the wireless transfer station 2210 based on received alignment information, wherein the alignment correction information directs the user how to increase the alignment of wireless transfer coil 2230 of the wireless transfer station 2210 relative to the wireless transfer coil of the other wireless transfer station. In another embodiment, the power management module 2260 can be configured to adjust an amount of energy transferred from the wireless transfer coil 2230 to a device or the other wireless transfer station and cease transferring wireless energy to the device or the other wireless transfer station 2210 or configure the wireless transfer station 2210 to enter a sleep mode when an energy transfer load of the wireless energy transfer decreases below a selected threshold.

Figure 23:
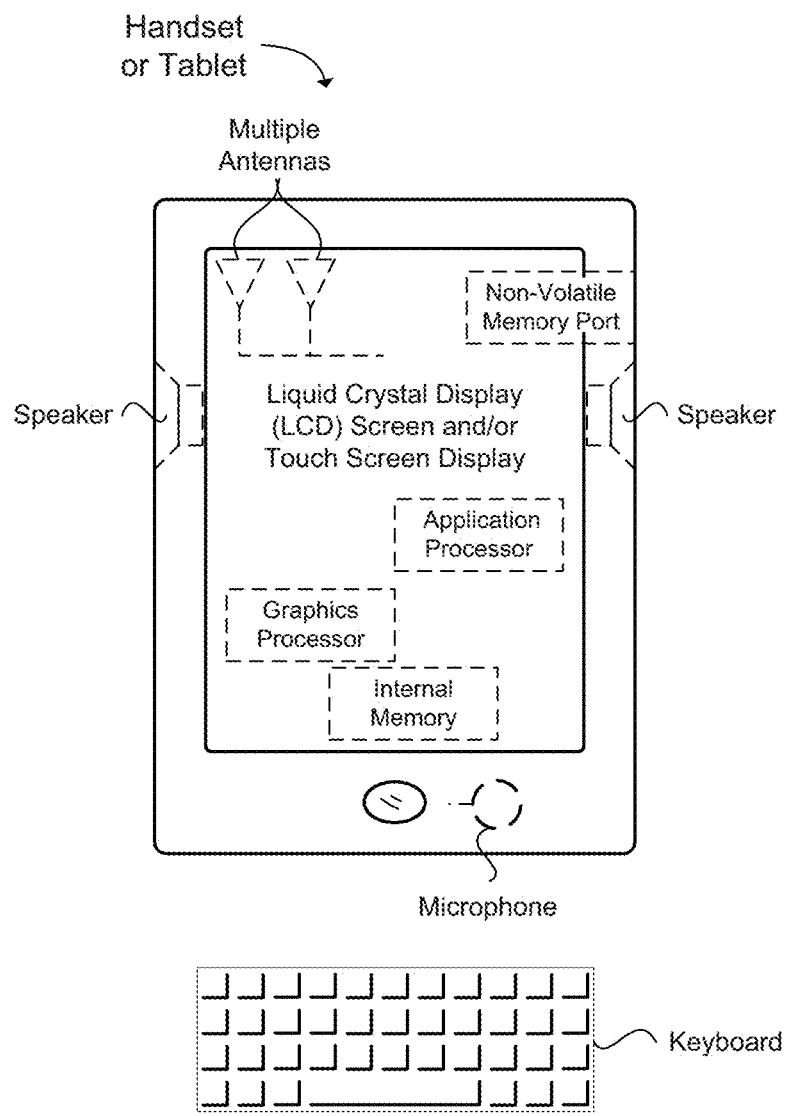
FIG. 23 illustrates a diagram of a device in accordance with an example.

FIG. 23 provides an example illustration of the device, such as a user equipment (UE), a mobile station (MS), a mobile wireless device, a mobile communication device, a tablet, a handset, or other type of device. The device can include one or more antennas configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device can be configured to communicate using at least one wireless communication standard including 3GPP LTE, WiMAX, High Speed Packet Access (HSPA), Bluetooth, and Wi-Fi. The device can communicate using separate antennas for each wireless communication standard or shared antennas for multiple wireless communication standards. The device can communicate in a wireless local area network (WLAN), a wireless personal area network (WPAN), and/or a WWAN.

FIG. 23 also provides an illustration of a microphone and one or more speakers that can be used for audio input and output from the device. The display screen may be a liquid crystal display (LCD) screen, or other type of display screen such as an organic light emitting diode (OLED) display. The display screen can be configured as a touch screen. The touch screen may use capacitive, resistive, or another type of touch screen technology. An application processor and a graphics processor can be coupled to internal memory to provide processing and display capabilities. A non-volatile memory port can also be used to provide data input/output options to a user. The non-volatile memory port may also be used to expand the memory capabilities of the device. A keyboard may be integrated with the device or wirelessly connected to the device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and examples of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A wheeled cart for wirelessly transferring energy, the wheeled cart, comprising:
   a wheeled cart;
   a work surface coupled to the wheeled cart;
   a first wireless transfer station integrated into the work surface, wherein the wireless transfer station comprises:
      a first wireless transfer platform; and
      a first wireless transfer coil located within the first wireless transfer platform for wirelessly transferring energy; and
      a first conversion module coupled to the first wireless transfer coil and configured to:
         switch the first wireless transfer coil between a transmit mode and a receive mode; and
         switch the first wireless transfer coil between a resonance charging mode and an induction charging mode.

2. The wheeled cart of claim 1, wherein the first wireless transfer station further comprises a battery.

3. The wheeled cart of claim 2, wherein the first wireless transfer station is operable to receive energy from another wireless transfer station to recharge the battery of the first wireless transfer station.

4. The wheeled cart of claim 2, further comprising an external wireless transfer station removable from the wheeled cart, wherein the external wireless transfer station comprises:
  a second wireless transfer platform; and
  a second wireless transfer coil located within the second wireless transfer platform for wirelessly transferring energy; and
  a second conversion module coupled to the second wireless transfer coil and configured to:
    switch the second wireless transfer coil between a transmit mode and a receive mode; and
    switch the second wireless transfer coil between a resonance charging mode and an induction charging mode.

5. The wheeled cart of claim 4, wherein the first wireless transfer station is operable to receive energy from the external wireless transfer station to recharge the battery of the first wireless transfer station.

6. The wheeled cart of claim 4, wherein the external wireless transfer station is operable to provide partial energy to the wheeled cart when the external wireless transfer station is receiving energy from another wireless transfer station.

7. The wheeled cart of claim 4, wherein the external wireless transfer station is operable to provide energy to the wheeled cart when the one external wireless transfer station is receiving energy from another wireless transfer station.

8. The wheeled cart of claim 4, wherein the first wireless transfer station is operable to receive power from another wireless transfer station when the external wireless transfer station is removed from the wheeled cart for recharging.

9. The wheeled cart of claim 4, wherein the external wireless transfer station is integrated into a removable wireless energy battery pack.

10. The wheeled cart of claim 9, wherein, when the removable wireless energy battery pack is removed from the wheeled cart for recharging, the first wireless transfer station provides power to the wheeled cart.

\* \* \* \* \*